(12) United States Patent
Brady-Kalnay et al.

(10) Patent No.: US 7,749,496 B2
(45) Date of Patent: Jul. 6, 2010

(54) NEURONAL REGENERATION

(75) Inventors: Susann Brady-Kalnay, Cleveland Heights, OH (US); Ravi V. Bellamkonda, Twinsburg, OH (US)

(73) Assignee: Case Western Reserve University, Cleveland, OH (US)

( * ) Notice: Subject to any disclaimer, the term of this patent is extended or adjusted under 35 U.S.C. 154(b) by 829 days.

(21) Appl. No.: 10/754,102

(22) Filed: Jan. 7, 2004

(65) Prior Publication Data
US 2004/0208862 A1    Oct. 21, 2004

Related U.S. Application Data

(63) Continuation-in-part of application No. PCT/US02/32942, filed on Oct. 15, 2002.

(60) Provisional application No. 60/329,155, filed on Oct. 12, 2001.

(51) Int. Cl.
*A61K 39/395* (2006.01)
*A61K 35/30* (2006.01)
*C07K 14/00* (2006.01)
*C07H 21/04* (2006.01)

(52) U.S. Cl. .................... 424/94.1; 424/570; 530/350; 536/23.5; 435/368

(58) Field of Classification Search ................ None
See application file for complete search history.

(56) References Cited

FOREIGN PATENT DOCUMENTS

| WO | WO 9602286 A1 * | 2/1996 |
|---|---|---|
| WO | WO 99/08533 A1 | 2/1999 |
| WO | WO 99/23113 A2 | 5/1999 |

OTHER PUBLICATIONS

Matsui and Oohira, Congenit Anom (Kyoto), 44: 181-8, 2004.*
Properzi et al., Biochem Soc Trans. 31: 335-6, 2003.*
Morgenstern et al., Prog Br Res 137: 313-32, 2002.*
Fenrich and Gordon, Can J Neurol Sc 31: 142-56, 2004.*
Brown et al., J Neurobiol 43: 352-364, 2000.*
Munemitsu et al., Mol and Cell Biol 10: 5977-5982, 1990.*
Miller and Johnson, Mol and Cell Biol 14: 1075-1083, 1994.*
Philips, Nervous system tissue engineering and culture modeling, online article, updated Apr. 2007.*
Yuan, Q, Review: Strategies for neuronal regeneration after spinal cord injury, 16: 1-8, 2007.*
Jin and Strittmatter, Jour Neurosc 17: 6256-6263, 1997.*
Gallo et al. Curr Biol 8: R80-R82, 1998.*
Shamah et al.Cell 105: 233-244, 2001.*
Abrams et al. Restor Neurol and Neurosc 23: 367-382, 2005.*
Halliday et al Clin Exp Pharmacol Physiol 27: 1-8, 2000.*
Steece-Collier et al., PNAS USA 99(22): 13972-13974, 2002.*
Feigin et al., Curr Opin Neurol 15: 483-489, 2002.*
Kozma et al., Mol Cell Biol 17: 1201-1211, 1997.*

Barker, R.A. et al. The Time Course of Loss of Dopaminergic Neurons and the Gliotic Reaction Surrounding Grafts of Embryonic Mesencephalon to the Striatum. Exp. Neurol. 141, 79-93 (1996).
Bradbury, E.J. et al. Chondroitinase ABC promotes functional recovery after spinal cord injury. Nature 416, 636640 (Apr. 11, 2002).
Burg, M.A. et al. Binding of the NG2 Proteoglycan to Type VI Collagen and Other Extracellular Matrix Molecules. J. Biol. Chem. 271, 26110-26116 (Oct. 18, 1996).
Davies, S.J.A. et al. Regeneration of adult axons in white matter tracts of the central nervous system. Nature 390, 680-683 (Dec. 1997).
Dergham, P. et al. Rho Signaling Pathway Targeted to Promote Spinal Cord Repair. J. Neurosci. 22(15), 6570-6577 (Aug. 1, 2002).
Drazba, J. and Lemmon, V. The Role of Cell Adhesion Molecules in Neurite Outgrowth on Muller Cells. Dev. Biol. 138, 82-93 (1990).
Fawcett, J.W. et al. The Growth of Axons in Three-Dimensional Astrocyte Cultures. Dev. Biol. 135, 449-458 (1989).
Fawcett, J.W. and Asher, R.A. The glial scar and central nervous system repair. Brain Res. Bull. 49(6), 377-391 (1999).
Fidler, P.S. et al. Comparing Astrocytic Cell Lines that Are Inhibitory or Permissive for Axon Growth: the Major Axon-Inhibitory Proteoglycan is NG2. J. Neurosci. 19(20), 8778-8788 (Oct. 15, 1999).
Fok-Seang, J. et al. An analysis of astrocytic cell lines with different abilities to promote axon growth. Brain Res. 689, 207-223 (1995).
Fournier, A.E. et al. Rho Kinase Inhibition Enhances Axonal Regeneration in the Injured CNS. J. Neurosci. 23(4), 1416-1423 (Feb. 15, 2003).
Friedlander, D.R. et al. The Neuronal Chondroitin Sulfate Proteoglycan Neurocan Binds to the Neural Cell Adhesion Molecules Ng-CAM/L1/NILE and N-Cam, and Inhibits Neuronal Adhesion and Neurite Outgrowth. J. Cell Biol. 125(3), 669-680 (May 1994).
Grumet, M. et al. Functions of Brain Chondroitin Sulfate Proteoglycans During Development: Interactions with Adhesion Molecules. Perspectives Dev. Neurobiol. 3, 319-330 (1996).
Halfter, W. et al. Oriented Axon Outgrowth from Avian Embryonic Retinae in Culture. Dev. Biol. 95, 56-64 (1983).
Hall, A. Small GTP-Binding Proteins and the Regulation of the Actin Ctyoskeleton. Annu. Rev. Cell Biol. 10, 31-54 (1994).
Hall, A. Rho GTPases and the Actin Cytoskeleton. Science 279, 509-514 (Jan. 23, 1998).
Hall, A. and Nobes, C.D. Rho GTPases: molecular switches that control the organization and dynamics of the actin cytoskeleton. Phil. Trans. R. Soc. Lond. 355, 965-970 (2000).

(Continued)

*Primary Examiner*—Jeffrey Stucker
*Assistant Examiner*—Aditi Dutt
(74) *Attorney, Agent, or Firm*—Tarolli, Sundheim, Covell & Tummino LLP

(57) ABSTRACT

A method of promoting neuronal regeneration includes administering an agent to at least one neural cell in contact with at least one neural cell growth inhibiting component in an amount effective to promote neuronal regeneration. The agent is selected from the group consisting of a Class I Rho family GTPase, a C1 activator, a Class II Rho family GTPase, and a C2 inhibitor.

9 Claims, 10 Drawing Sheets

OTHER PUBLICATIONS

Hoffman-Kim, D. et al. Patterns of Chondroitin Sulfate Immunoreactivity in the Developing Tectrum Reflect Regional Differences in Glycosaminoglycan Biosynthesis. J. Neurosci. 18(15), 5881-5890 (Aug. 1, 1998).

Kaibuchi, K. et al. Regulation of the Cytoskeleton and Cell Adhesion by the Rho Family GTPases in Mammalian Cells. Annu. Rev. Biochem. 68, 459-486 (1999).

Kottis, V. et al. Oligodendrocyte-myelin glycoprotein (OMgp) is an inhibitor of neurite outgrowth. J. Neurochem. 82, 1566-1569 (2002).

Kuhn, T.B. et al. Regulating Actin Dynamics in Neuronal Growth Cones by ADF/Cofilin and Rho Family GTPases. J. Neurobiol. 44, 126-144 (2000).

Luckenbill-Edds, L. Laminin and the mechanism of neuronal outgrowth. Brain Res. Rev. 23, 1-27 (1997).

Luo, L. et al. Distinct morphogenetic functions of similar small GTPases: Drosophila Drac1 is involved in axonal outgrowth and myoblast fusion. Genes & Dev. 8, 1787-1802 (1994).

Luo, L. Rho GTPases in Neuronal Morphogenesis. Nat. Rev. Neurosci. 1, 173-180 (Dec. 2000).

Margolis, R.U. And Margolis, R.K. Chondroitin sulfate proteoglycans as mediators of axon growth and pathfinding. Cell Tissue Res. 290, 343-348 (1997).

McKeon, R.J. et al. Injury-Induced Proteoglycans Inhibit the Potential for Laminin-Mediated Axon Growth on Astrocytic Scars. Exp. Neurol. 136, 32-43 (1995).

McKerracher, L. et al. Identification of Myelin-Associated Glycoprotein as a Major Myelin-Derived Inhibitor of Neurite Growth. Neuron 13, 805-811 (Oct. 1994).

Monnier, P.P. et al. The Rho/ROCK pathway mediates neurite growth-inhibitory activity associated with the chondroitin sulfate proteoglycans of the CNS glial scar. Mol. Cell. Neurosci. 22, 319-330 (2003).

Moon, L.D.F. et al. Regeneration of CNS axons back to their target following treatment of adult rat brain with chondroitinase ABC. Nat. Neurosci. 4(5), 465-466 (May 2001).

Morgenstern, D.A. et al. Chondroitin sulphate proteoglycans in the CNS injury response. Prog. Brain Res., L. McKerracher et al., eds. vol. 137, Ch. 22, 313-332 (2002).

Mukhopadhyay, G. et al. A Novel Role for Myelin-Asciated Glycoprotein as an Inhibitor of Axonal Regeneration. Neuron 13, 757-767 (Sep. 1994).

Niederost, B. et al. Nogo-A and Myelin-Associated Glycoprotein Mediate Neurite Growth Inhibition by Antagonistic Regulation of RhoA and Rac1. J. Neurosci. 22(23), 10368-10376 (Dec. 1, 2002).

Nikolic, M. The role of Rho GTPases and associated kinases in regulating neurite outgrowth. Int. J. Biochem. Cell Biol. 34, 731-745 (2002).

Nobes, C.D. and Hall, A. Rho, Rac, and Cdc42 GTPases Regulated the Assembly of Multimolecular Focal Complexes Associated with Actin Stress Fibers, Lamellipodia, and Filopodia. Cell 81, 53-62 (Apr. 7, 1995).

Qiu, J. et al. Glial Inhibition of Nerve Regeneration in the Mature Mammalian CNS. Glia 29, 166-174 (2000).

Ridley, A.J. Rho GTPases and cell migration. J. Cell Sci. 114, 2713-2722 (2001).

Sango, K. et al. Phosphacan and neurocan are repulsive substrata for adhesion and neurite extension of adult rat dorsal root ganglion neurons in vitro. Exp. Neurol. 182, 1-11 (2003).

Schmalfeldt, M. et al. Brain derived versican V2 is a potent inhibitor of axonal growth. J. Cell Sci. 113, 807-816 (2000).

Settleman, J. Rac 'n Rho: The Music that Shapes Developing Embryo. Dev. Cell 1, 321-331 (Sep. 2001).

Silver, J. Inhibitory molecules in development and regeneration. J. Neurol. 241, S22-S24 (1994).

Snow, D.M. et al. Sulfated Proteoglycans in Astroglial Barriers Inhibit Neurite Outgrowth in Vitro. Exp. Neurol. 109, 111-130 (1990).

Stichel, C.C. and Muller, H.W. The CNS lesion scar: new vistas on an old regeneration barrier. Cell Tissue Res. 294, 1-9 (1998).

Tang, B.L. Inhibitors of neuronal regeneration: mediators and signaling mechanisms. Neurochem. Int. 42, 189-203 (2003).

Vielmetter, J. et al. In vitro assay to test differential substrate affinities of growing axons and migratory cells. Exp. Brain Res. 81, 283-287 (1990).

Wittinghofer, A. and Nassar, N. How Ras-related proteins talk to their effectors. TIBS 21, 488-491 (Dec. 1996).

Yu, X. and Bellamkonda, R.V. Dorsal Root Ganglia Neurite Extension is Inhibited by Mechanical and Chondroitin Sulfate-Rich Interfaces. J. Neurosci. Res. 66, 303-310 (2001).

Zipkin, I.D. et al. Role of a New Rho Family Member in Cell Migration and Axon Guidance in C. elegans. Cell 90, 883-894 (Sep. 5, 1997).

Zuo, J. et al. Degradation of Chondroitin Sulfate Proteoglycan Enhances the Neurite-Promoting Potential of Spinal Cord Tissue. Exp. Neurol. 154, 654-662 (1998).

Lehmann, M. et al., "Inactivation of Rho Signaling Pathway Promotes CNS Axon Regeneration," The Journal of Neuroscience, Sep. 1, 1999, pp. 7537-7547, 19(17).

Sebök, A. et al., "Different Roles for RhoA During Neurite Initiation, Elongation, and Regeneration in PC12 Cells," Journal of Neurochemistry, pp. 949-960, vol. 73.

Tanabe, K. et al., "The Small GTP-Binding Protein TC10 Promotes Nerve Elongation in Neuronal Cells, and Its Expression Is induced during Nerve Regeneration in Rats," The Journal of Neuroscience, Jun. 1, 2000, pp. 4138-4144, 20(11).

Govek et al., "The Role of the Rho GTPases in neuronal development", *Genes and Development* 19:1-49, ISSN: 0890-9369/05, 2005.

Meyer et al., "Signaling mechanisms that regulate actin-based motility processes in the nervous system", *Journal of Neurochemistry*, 2002, 83, 490-503.

* cited by examiner

NEURONAL REGENERATION

RELATED APPLICATIONS

This application is a continuation-in-part of and claims priority to PCT/US02/32942, filed Oct. 15, 2002, and U.S. provisional application 60/329,155 filed Oct. 12, 2001, the disclosures of which are hereby incorporated by reference in their entirety.

BACKGROUND OF THE INVENTION

One of the greatest obstacles in developing effective treatment for injuries and degenerative diseases of the nervous system is the poor regenerative capacity of neuronal cells. Regeneration of neuronal cells in the central nervous system is currently not possible, and although neuronal cells in the peripheral nervous system show some regenerative capacity, this occurs very slowly across limited nerve gaps. Thus, individuals who experience reduction in neuronal function following injury or diseases of the central nervous system typically see little or no improvement in their condition over time, while individuals experiencing reduction in neuronal function following injury or disease of the peripheral nervous system may experience some improvement, but only after a considerable period of time. Accordingly, there exists a need for improved methods and compositions to promote neuronal regeneration in the central and peripheral nervous systems.

Neurons have cellular processes called axons that migrate and establish connections with their targets. One of the results of damage to the nervous system is the formation of glial scar tissue. Glial scar tissue is composed of astrocytes, oligodendrocytes and microglia, as well as a rich meshwork of extracellular matrix proteins including proteoglycans. Glial scar tissue formed in response to cellular damage presents a physical and/or a molecular barrier to regeneration. The content of glial scar tissue is complex, and thus the inhibitory effects of glial scar tissue may be due to multiple components of the scar. Proteoglycans are molecules consisting of one or more glycosaminoglycan (GAG) chains attached to a core protein. For example, it has been demonstrated that chondroitin sulfate proteoglycans (CSPGs) and chondroitin sulfate glycosaminoglycans (CS-GAGs), which are found in the glial scar, are inhibitory to regenerating neurons (reviewed in Silver (1994) *J Neurol.* 242: S22-4; Yu and Bellamkonda (2001) *J. Neurosci. Res.* 66: 303-310). These studies indicate that chondroitin sulfate GAGs play a role in the inhibitory effects of glial scar tissue, and additional studies suggest that the protein core of CSPGs may also play a role in inhibiting regeneration (Margolis and Margolis (1997) *Cell Tissue Res.* 290: 343-8; Friedlander et al. (1994) *J. Cell Biol.* 125: 669-680).

In addition to the inhibitory effects on regeneration mediated by glial scarring, a number of other factors may influence the rate and extent of regeneration in both the central nervous system and the peripheral nervous system. For example, inflammation is a common cellular response to trauma including trauma caused by physical injury, chemical assault, disease, and the like. Furthermore, the ability of cells to respond to local cues may be inhibited either transiently or permanently following trauma. Cells can literally be shocked by injury or disease, and thus be unable to respond to local cues including cues which may facilitate regeneration following injury.

Regardless of the mechanism underlying inhibition of neuronal regeneration following injury and disease, there exists a need to develop methods and compositions to promote regeneration. The present invention provides such methods and compositions. Given that there currently exists no effective method of promoting neuronal regeneration, the present invention addresses a crucial and currently unmet need.

SUMMARY OF THE INVENTION

The methods and compositions described in the present application address the need in the art for improved methods of promoting neuronal regeneration. In a first aspect, the present invention provides a method of promoting neuronal regeneration, comprising administering an agent in an amount effective to promote neuronal regeneration.

In one embodiment, the agent is selected from the group consisting of a Class I Rho family GTPase, a C1 activator, a Class II family Rho GTPase, and a C2 inhibitor. In another embodiment, the agent is a Class I Rho family GTPase selected from the group consisting of a Rac, Cdc42, and Rho.

In another embodiment, the Class I Rho family G TPase is a constitutively active Cdc42 variant. In another embodiment, the constitutively active Cdc42 variant comprises a Q61L mutation in SEQ ID No:2 or a G12V mutation in SEQ ID No:2.

In another embodiment, the Class I Rho family G TPase is a constitutively active Rac1 variant. In yet another embodiment, the constitutively active Rac1 variant comprises a Q61L mutation in SEQ ID No: 4 or a G12V mutation in SEQ ID No: 4.

In another aspect, the Class I Rho family GTPase is a constitutively active Rho variant. In still another embodiment, the constitutively active Rho variant comprises a Q63L mutation in SEQ ID No: 6 or a G14V mutation in SEQ ID No: 6.

In a second aspect, the agent is a Class II family Rho GTPase selected from the group consisting of a Rac, Cdc42, and Rho. In another embodiment, the Class II Rho family GTPase is a dominant negative Cdc42 variant. In yet another embodiment, the Cdc42 variant comprises a T17N mutation in SEQ ID No:2.

In a further embodiment, the Class II Rho family GTPase is a dominant negative Rac1 variant. In another embodiment, the dominant negative Rac1 variant comprises a T17N mutation in SEQ ID No: 4.

In yet another embodiment, the Class II Rho family GTPase is a dominant negative Rho variant. In still another embodiment, the dominant negative Rho variant comprises a T19N mutation in SEQ ID No: 6.

In a third aspect, the agent is a C1 activator. In yet another embodiment, the C1 activator is selected from the group consisting of small organic molecules that increase expression of a Class I Rho family GTPase, small organic molecules that increase the "on" state of a Class I Rho family GTPase, agents which decrease the expression or activity of GTPase-activating proteins (GAPs), and agents which increase the expression or activity of Guanine nucleotide exchange factors (GEFs).

In a fourth aspect, the agent is a C2 inhibitor. In yet another embodiment, the C2 inhibitor is selected from the group consisting of RNAi oligonucleotides or constructs that decrease the expression of a Class II Rho family GTPase, antibodies that promote the "off" state of a Class II Rho family GTPase, small organic molecules that decrease expression of a Class II Rho family GTPase, small organic molecules that promote the "off" state of a Class II Rho family GTPase, antisense oligonucleotides or constructs that decrease the expression of a Class II Rho family GTPase, agents which increase the expression or activity of GTPase-activating proteins (GAPs), and agents which decrease the expression or activity of Guanine nucleotide exchange factors (GEFs).

In any of the foregoing aspects, the invention further contemplates that neuronal regeneration may occur at a glial scar. In one embodiment, the glial scar is a proteoglycan rich glial scar. In another embodiment, the proteoglycan rich glial scar comprises one or more of chondroitin sulfate proteoglycans or chondroitin sulfate glycosaminoglycans.

In another embodiment, the glial scar is in the central nervous system. In another embodiment, the glial scar is the result of physical injury.

In any of the foregoing aspects, the invention further contemplates that agents may be administered in combination with one or more neurotrophic factors or growth factors. In one embodiment, the neurotrophic factor or growth factor is selected from at least one of nerve growth factor (NGF), basic fibroblast growth factor (bFGF), brain-derived growth factor (BDGF), neurotrophin 3 (NT-3), neurotrophin 4 (NT-4), neurotrophin 5 (NT-S), glial derived neurotrophic factor (GDNF) or ciliary neurotrophic factor (CNTF).

In another embodiment, agents may be administered in combination with an enzyme that digests proteoglycan sugars.

In a fifth aspect, the present invention provides a method of treating an injury or degenerative disease of the central or peripheral nervous system of a mammal, comprising administering to said mammal an amount of an agent effective to promote neuronal regeneration, wherein said agent is a Class I activator.

In one embodiment, the mammal is a human.

In another aspect, the method further comprises administering a neurotrophic factor or growth factor. In another embodiment, the neurotrophic factor or growth factor is selected from at least one of nerve growth factor (NGF), basic fibroblast growth factor (bFGF), brain-derived growth factor (BDGF), neurotrophin 3 (NT-3), neurotrophin 4 (NT-4), neurotrophin 5 (NT-5), glial derived neurotrophic factor (GDNF) or ciliary neurotrophic factor (CNTF).

In still another embodiment, the method further comprises administering an enzyme that digests proteoglycan sugars.

In a sixth aspect, the present invention provides a method of treating an injury or degenerative disease of the central or peripheral nervous system of a mammal, comprising administering to said mammal an amount of an agent effective to promote neuronal regeneration, wherein said agent is a Class II inhibitor.

In one embodiment, the mammal is a human.

In one embodiment, the method further comprises administering a neurotrophic factor or growth factor. In another embodiment, the neurotrophic factor or growth factor is selected from at least one of nerve growth factor (NGF), basic fibroblast growth factor (bFGF), brain-derived growth factor (BDGF), neurotrophin 3 (NT-3), neurotrophin 4 (NT-4), neurotrophin 5 (NT-5), glial derived neurotrophic factor (GDNF) or ciliary neurotrophic factor (CNTF).

In still another embodiment, the method further comprises administering an enzyme that digests proteoglycan sugars.

In a seventh aspect, the present invention provides a method of treating an injury or degenerative disease of the central or peripheral nervous system of a mammal, comprising administering to said mammal an amount of a Class I Rho family GTPase, an activated (constitutively active) Class I Rho family GTPase or an C1 activator effective to promote neuronal regeneration.

In one embodiment, the mammal is a human.

In one embodiment, the method further comprises administering a neurotrophic factor or growth factor. In another embodiment, the neurotrophic factor or growth factor is selected from at least one of nerve growth factor (NGF), basic fibroblast growth factor (bFGF), brain-derived growth factor (BDGF), neurotrophin 3 (NT-3), neurotrophin 4 (NT-4), neurotrophin 5 (NT-5), glial derived neurotrophic factor (GDNF) or ciliary neurotrophic factor (CNTF).

In still another embodiment, the method further comprises administering an enzyme that digests proteoglycan sugars.

In an eighth aspect, the present invention provides a method of treating an injury or degenerative disease of the central or peripheral nervous system of a mammal, comprising administering to said mammal an amount of a Class II Rho family GTPase or a dominant negative Class II Rho family GTPase effective to promote neuronal regeneration.

In one embodiment, the mammal is a human.

In one embodiment, the method further comprises administering a neurotrophic factor or growth factor. In another embodiment, the neurotrophic factor or growth factor is selected from at least one of nerve growth factor (NGF), basic fibroblast growth factor (bFGF), brain-derived growth factor (BDGF), neurotrophin 3 (NT-3), neurotrophin 4 (NT-4), neurotrophin 5 (NT-S), glial derived neurotrophic factor (GDNF) or ciliary neurotrophic factor (CNTF).

In still another embodiment, the method further comprises administering an enzyme that digests proteoglycan sugars.

In a ninth aspect, the present invention provides a method of identifying an agent that promotes neuronal regeneration. In one embodiment, the invention provides a method of identifying an agent that promotes neuronal regeneration, comprising culturing neuronal cells in a three-dimensional gel containing a neuronal regeneration inhibitory substance, and determining neuronal regeneration in the presence of said agent. In the context of this method, an increase in neuronal extension indicates that said agent promotes neuronal regeneration.

In another embodiment, the invention provides a method of identifying an agent that promotes neuronal regeneration, comprising culturing neuronal cells on a substrate coated with a neuronal regeneration inhibitory substance at predetermined regions of said substrate, adding an agent to said substrate, and determining neuronal regeneration at the regions coated with the neuronal regeneration inhibitory substance in the presence of said agent. In the context of this method, an increase in neuronal extension at said predetermined region indicates that said agent promotes neuronal regeneration.

In any of the foregoing methods, the inhibitory substance may be chondroitin sulfate proteoglycans or chondrotin sulfate glycosaminoglycans.

In a tenth aspect, the present invention features pharmaceutical preparations comprising a C1 activator, a C2 inhibitor, or any agent identified by the methods of the present invention. The pharmaceutical preparations comprise an agent formulated in a pharmaceutically acceptable carrier or excipient.

In an eleventh aspect, the present invention provides a method of treating an injury or degenerative disease of the nervous system by administering an effective amount of a C1 activator or C2 inhibitor.

The practice of the present invention will employ, unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999.

Other features and advantages of the invention will be apparent from the following detailed description, and from the claims.

BRIEF DESCRIPTION OF THE DRAWINGS

FIG. 1 specifically shows a three dimensional gel where layer 1 comprises agarose (a control interface), layer 2 contains dorsal root ganglia (DRGs) in agarose, and layer three is an agarose layer containing CS-GAG. The layer 1/layer 2 interface provides a control agarose/agarose interface, while the layer 2/layer 3 interface provides an agarose/CS-GAG rich agarose interface.

FIG. 2A shows an E9 Chick DRG extending processes in a 3D agarose gel culture. FIG. 2B summarizes the three-dimensional agarose gel culture system outlined in detail in FIG. 1. FIG. 2C shows that extension of neuronal processes from E9 chick DRG was inhibited at the 3D interface between layer 2 and layer 3. Specifically, neuronal processes from DRGs cultured in layer 2 (1% agarose) extend, however this extension was inhibited when the processes contacted the layer 2/layer 3 interface where the layer 3 interface contains 2% agarose modified with chondroitin sulfate B.

FIG. 4A summarizes the results of experiments in which E4 chick retina were cultured in chondroitin sulfate GAG modified agarose gel. The length of the processes extending from the explant were measured. The right most bar indicates that retina cultured in chondroitin sulfate GAGs extended only short processes. The left most bar indicates that infection of E4 chick retina with retrovirus encoding constitutively active Cdc42 significantly increases the length of the processes in the presence of chondroitin sulfate. For this experiment, the constitutively active Cdc42 variant used was the Q61L mutation of human Cdc42 (Q61 L mutation of SEQ ID NO: 2). FIG. 4B provides a photo of a retinal explant cultured in the presence of CS-GAG. Neurite outgrowth from the explant is inhibited in the presence of CS-GAG. FIG. 4C provides a photo of retinal explants infected with constitutively active Cdc42 cultured in the presence of CS-GAG.

FIG. 5A provides a graph which shows that less than 10% of unmodified NG108 cells crossed the short axis of a chondroitin sulfate GAGs containing coverslip. However, approximately 50% of NG108 cells where constituitively active Rho family GTPase (constituitively active Cdc42) was added by protein transduction crossed the short axis. In these experiments, constituitively active Cdc42 protein was delivered to NG108 cells directly using the Chariot™ protein transduction system. FIG. 5B shows a picture (10× magnification) of unmodified NG108 cells approximately 48 hours after seeding of the cells onto the chondroitin sulfate GAGs containing coverslips. Note that the cells align a long the long axis, and do not extend processes a long the short axis. FIG. 5C shows a picture (10× magnification) of constituitively active Cdc42 expressing NG108 cells. Note the extensive neuronal processes along the short axis.

BEST MODE FOR CARRYING OUT THE INVENTION

Detailed Description of the Invention

(i) Overview

Figure 1:
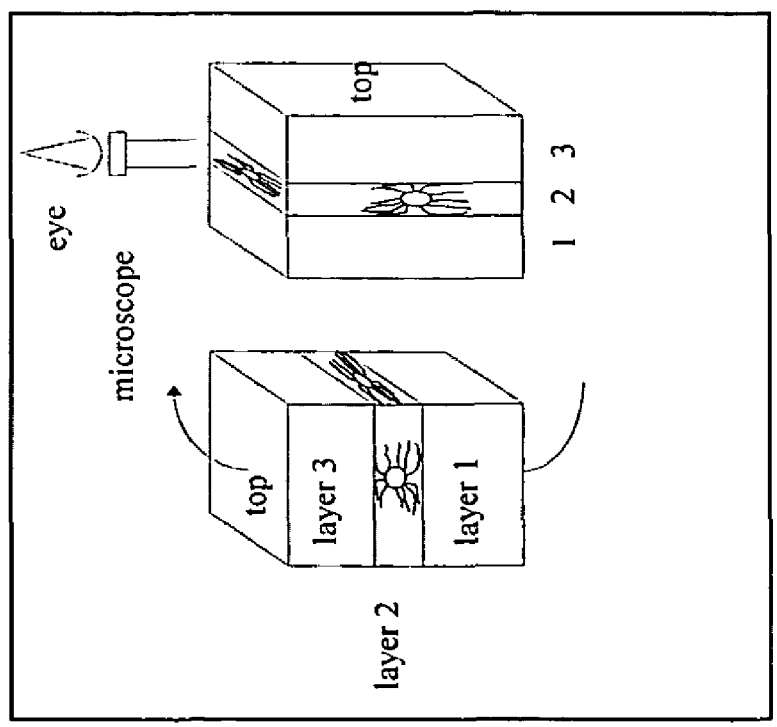
FIG. 1 shows serial layering of agarose gels using custom-built glass cubic dishes. This three-dimensional system allows observation of neuronal cell behavior at gel interfaces.

The human body has tremendous regenerative capacity. However, despite the generally robust healing prowess of our bodies, neuronal tissue appears to have relatively poor regenerative capacity. In the central nervous system, cell damage frequently results in the formation of a glial scar, and this glial scar provides a physical and/or molecular barrier to regeneration. Additionally, injuries and diseases in the central nervous system often cause local inflammation and trauma that inhibit regeneration by mechanisms that are not entirely clear. The inhibition of regeneration following injury and/or diseases of the central nervous system hampers recovery from a wide range of conditions including physical injuries to the brain or spinal cord, infections, brain or spinal cord surgery, stroke, Parkinson's disease, Huntington's disease, ALS, Alzheimer's disease, multiple sclerosis, detached retina, and macular degeneration. The ability to promote neuronal regeneration in the central nervous system would provide improved treatment options for patients afflicted with any of these conditions.

Neuronal cells of the peripheral nervous system show some limited capacity to regenerate following injury or disease. However, this regeneration occurs very slowly, and does not typically result in the restoration of total pre-injury or pre-disease function. Thus, the ability to increase the rate or extent of neuronal regeneration in the peripheral nervous system following injury or disease would greatly improve the recovery of patients afflicted with any of a number of injuries or diseases of the peripheral nervous system. Such conditions include physical injuries to cells of the peripheral nervous system, infections, neuropathy, and diabetic neuropathy.

Given that injured and diseased neuronal tissue typically exhibits low regenerative capacity, there exists a need for improved methods of promoting neuronal regeneration in cells of the central and peripheral nervous system. The present invention provides methods and compositions for promoting neuronal regeneration. The methods and compositions provided herein promote neuronal regeneration following a wide range of injuries and disease states. In one example, the methods and compositions promote neuronal regeneration through a glial rich scar. In another example, the methods and compositions promote neuronal regeneration following, or in the presence of, inflammation. In still another example, the methods and compositions promote neuronal regeneration in the presence of a neurodegenerative disease.

The methods and compositions disclosed in this application are based on altering the activity of Rho family GTPases in neuronal cells of the central or peripheral nervous system. Briefly, Rho family GTPases represent a point of convergence for extracellular signals that modulate the actin cytoskeleton. Rho family GTPases, including Rho, Rac and Cdc42, regulate the actin cytoskeleton (reviewed in Hall and Nobes (2000) *Philos Trans R Soc Lond B Biol Sci.* 355: 965-70; Luo et al. (2000) *Nature Rev. Neurosci.* 1: 173-180). Wild type Rho family GTPases cycle between two biochemical states characterized by association with either GDP or GTP. The GTP bound state is the "on" state and the GDP bound state is the "off" state, and Rho family GTPases will exert varying effects on cells in their "on" or "off" conformation. The "on" or "off" state is regulated, at least in part, by several other classes of proteins including guanine nucleotide exchange factors (GEFs), GTPase activating proteins (GAPs), and GTP dissociation inhibitors (GDIs). GEFs act to facilitate the release of GDP and the subsequent binding of GTP, and thus promote the "on" state of Rho family GTPases. GAPs function to stimulate the intrinsic GTP hydrolyzing activity of Rho family GTPases, and thus promote the "off" state. GDIs often act as negative regulators by preventing the dissociation of GDP from Rho family GTPases, and thus promote the "off" state.

A large number of GEFs, GAPs, and GDIs exist. Some of these are expressed specifically in certain tissues or cell types. For example, the GEFs Kalirin, Ost, Stef and Tiam, the GAPs p190RhoGAP, α-chimaerin, and oligophrenin-1, and the GDI RhoGDIγ, are all enriched in the nervous system. Additionally, it is known that some GEFs, GAPs, and GDIs preferentially regulate a particular Rho family GTPase, while other GEFs, GAPs, and GDIs can regulate more than one Rho family GTPase, and still other GEFs, GAPs, and GDIs can regulate many Rho family GTPases (Nikolic (2002) *International Journal of Biochemistry and Cell Biology* 34: 731-745; Settleman (2001) *Developmental Cell* 1: 321-331).

Rho family GTPases are involved in transducing extracellular cues that modulate neuronal growth and behavior (reviewed in Kuhn et al. (2000) *J Neurobiol.* 44: 126-44). Without wishing to be bound by theory, the mechanisms used to overcome inhibition of neuronal regeneration may include modulating the signal transduction pathways used by cells to regulate neuronal growth. Accordingly, the present invention provides methods and compositions that promote neuronal regeneration. Agents for use in the subject methods include agents that promote the "on" state of a class of Rho family GTPases, and thus promote neuronal regeneration. Agents for use in the subject methods further include agents that promote the "off" state of a second class of Rho family GTPases, and thus promote neuronal regeneration.

Agents which promote neuronal regeneration in the central or peripheral nervous system have utility in treating injuries and diseases of the central and peripheral nervous system. Therefore, the present invention contemplates methods of treating injuries and diseases of the central and peripheral nervous system.

The invention further contemplates methods of screening for agents which promote the "on" state or the "off" state of Rho family GTPases. Such agents, including nucleic acids, peptides, polypeptides, peptidometics, antisense constructs or oligonucleotides, RNAi constructs or oligonucleotides, antibodies, small organic molecules, and the like, can be identified based on their ability to promote neuronal regeneration. Agents identified by the screening methods disclosed herein may be used to promote neuronal regeneration in the central nervous system or the peripheral nervous system.

(ii) Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

As used herein, "glial scar" refers to the reactive gliosis which occurs following injury or degeneration of a neuron in the central nervous system. The scar is composed of both glial cells and many extracellular matrix molecules including proteoglycans.

The terms "glial scar" and "proteoglycan rich glial scar" are used interchangeably throughout this application. Gliosis or glial scarring following tissue injury inhibits regeneration of cells of the central nervous system following injury and other cell damage such as cell damage caused by degenerative disease. Without being bound by theory, glial scarring is thought to provide a physical and/or molecular barrier to regeneration. Exemplary proteoglycan rich glial scars comprise sulfated proteoglycans such as chondroitin sulfate proteoglycans.

As used herein, "proteoglycan" refers to proteins modified to include one or more polysaccharide (sugar) moieties. Glycosaminoglycans are the polysaccharide chains of proteoglycans, and contain repeating units of disaccharides that consist of an amino sugar derivative, either glucosamine or galactosamine. A negatively charged carboxylate or sulfate group is found in at least one of the sugar units of the disaccharide. The term proteoglycan does not refer to a single protein or to a set of proteins that share a high degree of amino acid identity. Rather, the term is used to refer to a heterogeneous "family" of proteins which may share little amino acid similarity with respect to the core protein. Proteoglycans are found in abundance in extracellular matrix and in healthy tissues including connective tissue. Additionally, a variety of studies have demonstrated that glial scars are rich in a number of extracellular matrix proteins including proteoglycans (Stichel and Muller (1998) *Cell Tissue Research* 294: 1-9). Extracellular matrix proteins and proteoglycans found in glial scars include, without limitation, collagen IV, laminin, fibronectin, chondroitin sulfate proteoglycans, heparin sulfate proteoglycans, keratin sulfate proteoglycans, and thrombospondin.

As used herein, "chondroitin sulfate proteoglycans (CSPGs)" and "chondroitin sulfate glycosaminoglycans (CS-GAGs)" refer to a heterogenous family of proteoglycans, as well as a heterogeneous family of glycosaminoglycan modifications. One of skill in the art will recognize that such proteoglycans are loosely classified based on modification, and the core proteins vary largely in terms of linear amino acid sequence. Additionally the extent of glycosylation can vary greatly among these proteoglycans. Examples of chondroitin sulfate proteoglycans are well known in the art, and the amino acid sequence corresponding to the core protein of many of these CSPGs has been determined in different mammalian species. Exemplary CSPGs include versican/CSPG2 [Gen Bank Accession Nos. NM_004385 (human), NM_019389 (mouse)], aggregan/CSPG1 [GenBank Accession Nos. NM_001135 (human), NM_013227 (human), NM_022190 (rat)], bamacan/CSPG6 [GenBank Accession Nos. NM_005445 (human), NM_031583 (rat), NM_007790 (mouse)], CSPG4 [GenBank Accession Nos. NM_001897 (human), NM_139001 (mouse)], brevican [GenBank Accession Nos. NM_021948 (human), NM_012916 (rat)], neuroglycanC/CSPG5 [GenBank Accession Nos. NM_006574 (human), NM_019284 (rat), NM_013884 (mouse)], neurocan/CSPG3 [GenBank Accession Nos. NM_004386 (human), NM_031653 (rat), NM_007789 (mouse)], leprecan [GenBank Accession Nos. AF087433 (rat)], and phosphacan [GenBank Accession Nos. U04998 (rat)]. Furthermore, chondroitin sulfate proteoglycans can potentially be composed of at least five different types of chondroitin sulfate-glycosaminoglycan (CS-GAG) chains (known as CS-GAGs A, B, C, D, and E), that differ from each other by the number and type of individual disaccharide moieties.

As used herein, "Rho family GTPase" refers to a broad class of proteins that have intrinsic GTPase activity (reviewed in Wittinghofer and N assar (1996) TIBS 21: 488-491; Ridley (2001) *Journal of Cell Science* 114: 2713-2722; Nikolic et al. (2002) *International Journal of Biochemistry and Cell Biology* 34: 731-745). Intrinsic GTPase activity means that members of this family bind to GTP and convert GTP to GDP. These proteins function as molecular switches. For the native enzymes, in the GTP bound form they are in an active conformation or "on" state and are able to interact with a set of downstream effectors. In their GDP bound state they are in an "off" conformation or state and may bind to a different set of proteins. Mutants can be generated to make the Rho family GTPase constituitively active or function in a dominant negative capacity. These mutants may be preferentially GTP or GDP bound, respectively. However in some cases, the mutants can assume the "on" or "off" state independent of nucleotide binding.

Exemplary Rho family GTPases include Cdc42, Rac1, and RhoA. A number of other classes of molecules interact with Rho family GTPases to promote either the GTP or GDP bound states including guanine nucleotide exchange factors (GEFs), GTPase activating proteins (GAPs), and GTP dissociation inhibitors (GDIs). GEFs act to facilitate the release of GDP and the subsequent rebinding of GTP, and act to promote the "on" state (activated or constitutively active) of Rho family GTPases. GAPs function to stimulate the intrinsic GTP hydrolyzing activity of Rho family GTPases, and thus act to promote the "off" state. GDIs often act as negative regulators by preventing the dissociation of GDP from Rho family GTPases, and thus promote the "off" state.

An agent which promotes or increases the active conformation or the "on" state of a Rho family GTPase will be referred to as an "activator". Such agents may include constitutively active mutant forms of the Rho family GTPases, wherein the mutant mimics the active or "on state." An agent which promotes the "off" state, whether by actively promoting the "off" state or by inhibiting the "on" state, will be referred to as an "inhibitor". Such agents may include dominant negative mutant forms of the Rho family GTPases, wherein the mutant promotes the "off state".

As used herein, Rho family GTPases can be subdivided into two classes based on their activity in the methods of the present invention. The term "Class I" or "Activator Class" is used to refer to Rho family GTPases which, in their active or "on" state, promote neuronal regeneration. Exemplary members of Class I Rho family GTPases include a polypeptide having an amino acid sequence that is at least 80%, 90%, 95%, 97%, 98%, 99%, or 100% identical to an amino acid sequence as set forth in SEQ ID Nos: 2, 4, and 6. In one embodiment this class would include constitutively active mutants of a Rho family GTPase.

The term "Class II" or "Inhibitory Class" refers to Rho family GTPases which, in their "off" state, promote neuronal regeneration. Exemplary members of Class II Rho family GTPases include a polypeptide having an amino acid sequence that is at least 80%, 85%, 90%, 95%, 97%, 98%, 99%, or 100% identical to an amino acid sequence as set forth in SEQ ID Nos: 2, 4, and 6. In one embodiment this class would include dominant negative mutants of a Rho family GTPase.

The term "agent" refers to a compound used in the methods of the present invention to promote neuronal regeneration, as well as to a compound screened by the methods of the present invention. The term agent includes nucleic acids, peptides, proteins, peptidomimetics, small organic molecules, chemical compounds, ribozymes, RNAi constructs (including siRNA), antisense RNAs, and antibodies. Preferred agents for use in the subject methods are those which promote neuronal regeneration. Preferred agents may be broadly divided into two classes based on the Rho family GTPase members which they influence. The first subset of agents are those which increase the "on state" of a Class I Rho family GTPase. Such agents will also be referred to as "C1 activators", and such C1 activators increase the activity (promote the "on" state) of a Class I Rho family GTPase. The second subclass of agents are those which suppress the activity (promote the "off" state) of a Class II Rho family GTPase. Such agents will also be referred to as "C2 inhibitors", and such C2 inhibitors suppress the activity (promote the "off" state) of a Class II Rho family GTPase. One of skill in the art will recognize that both C1 activators and C2 inhibitors can influence Rho family GTPase activity by any of a number of mechanisms. Such mechanisms will be discussed in greater detail below.

Agents used in the methods described herein, as well as agents screened by the methods described herein can be administered and/or screened individually, or can be administered in combination with one or more other agents. Exemplary combinations include (i) two or more C1 activators, (ii) two or more C2 inhibitors, (iii) one or more C1 activators and one or more C2 inhibitors, (iv) one or more C1 activators and one or more neurotrophic factors or growth factors, (v) one or more C2 inhibitors and one or more neurotrophic factors or growth factors, (vi) one or more C1 activators, one or more C2 inhibitors, and one or more neurotrophic factors or growth factors, (vii) one or more C1 activators and one or more proteoglycan specific enzymes, (viii) one or more C2 inhibitors and one or more proteoglycan specific enzymes, and (ix) one or more C1 activators, one or more C2 inhibitors, and one or more proteoglycan specific enzymes.

The invention further contemplates the screening of libraries of agents. Such libraries may include, without limitation, cDNA libraries (either plasmid based or phage based), expression libraries, combinatorial libraries, chemical libraries, phage display libraries, variegated libraries, and biased libraries. The term "library" refers to a collection of nucleic acids, proteins, peptides, chemical compounds, small organic molecules, or antibodies. Libraries comprising each of these are well known in the art. Exemplary types of libraries include combinatorial, variegated, biased, and unbiased libraries. Libraries can provide a systematic way to screen large numbers of nucleic acids, proteins, peptides, chemical compounds, small organic molecules, or antibodies. Often, libraries are sub-divided into pools containing some fraction of the total species represented in the entire library. These pools can then be screened to identify fractions containing the desired activity. The pools can be further subdivided, and this process can be repeated until either (i) the desired activity can be correlated with a specific species contained within the library, or (ii) the desired activity is lost during further subdivision of the pool of species, and thus is the result of multiple species contained within the library.

As used herein, "neurotrophic factor" or "growth factor" refers to any of a number of proteins known in the art that have been demonstrated to promote neuronal survival. Without being bound by theory, it is believed that neuronal survival is influenced by the presence of survival factors, and that these survival factors are present in quantities which limit the number of neurons which can survive. The remaining neurons, which appear to be otherwise normal and healthy, die. Exemplary neurotrophic factors include, without limitation, nerve growth factor (NGF), brain-derived growth factor (BDGF), neurotrophin 3 (NT-3), neurotrophin 4 (N-4), neurotrophin 5 (NT-5), glial derived neurotrophic factor (GDNF), and ciliary neurotrophic factor (CNTF). Exemplary growth factors include basic fibroblast growth factor (bFGF).

As used herein, "dominant negative" refers to variant forms of a protein that inhibit the activity of the endogenous, wild type form of the protein. As a result, the dominant negative promotes the "off" state. In the context of the present invention, a dominant negative Rho family GTPase is a Rho family GTPase which has been modified (e.g., by mutation of one or more amino acid residues, by posttranscriptional modification, by posttranslational modification) such that the modified Rho family GTPase inhibits the activity of the endogenous Rho family GTPase and thus promotes the "off" state. By way of example, dominant negative Rho family GTPases include: T17N mutation in Rac1, T19N mutation in RhoA, and T17N mutation in Cdc42.

As used herein, "activated Rho family GTPase" refers to a variant form of a Rho family GTPase which is either constitutively active or increases the "on" state in comparison to the wild type Rho family GTPase. By way of example, activated Rho family GTPases include: Q61L mutation in Rac1, Q63L mutation in RhoA, Q61L mutation in Cdc42, G12V mutation in Rac1, G14V mutation in RhoA, and the G12V mutation in Cdc42.

"Regeneration" of neurons and "neuronal regeneration" are used interchangeably throughout and refer to the promotion of neuronal cell growth, and/or neuronal survival following injury or cell damage. The term neuronal cell growth is meant to include extension of cellular processes including axons and dendrites. By regeneration is meant to include promotion of neuronal cell survival and/or neuronal cell growth at the site of injury (e.g., survival or growth of the injured cell itself), as well as promotion of neuronal cell survival and/or neuronal cell growth at some distance from, but in response to, the injury or cell damage.

As used herein, "neuronal cell" or "cell of the nervous system" include both neurons and glial cells.

As used herein, "CNS neuron" refers to a neuron whose cell body is located in the central nervous system. The term is also meant to encompass neurons whose cell body was originally located in the central nervous system (e.g., endogenously located in the CNS), but which have been explanted and cultured ex vivo, as well as the progeny of such cells. Examples of such neurons are motor neurons, interneurons and sensory neurons including retinal ganglion cells, dorsal root ganglion cells and neurons of the spinal cord.

As used herein, "central nervous system" refers to any of the functional regions of the brain or spinal cord. This definition is used commonly in the art and is based, at least in part, on the common embryonic origin of the structures of the brain and spinal cord from the neural tube.

The "peripheral nervous system" can be distinguished from the central nervous system, at least in part, by its differing origin during embryogenesis. Cells of the peripheral nervous system are derived from the neural crest and include neurons and glia of the sensory, sympathetic and parasympathetic systems.

As used herein, "soma" refers to the cell body of a neuron.

As used herein, "axon" and "neurite" are used interchangeably to refer to the single outgrowth which extends from a neuron and which will ultimately migrate to innervate a target tissue. The tip of the axon is referred to as the "growth cone". Axons extend from a neuron to a target tissue, and are capable of conducting impulses. In the literature, the term "axon" is often used to refer to the outgrowth from a cell in vivo, and the term "neurite" is often used to refer to the outgrowth from a cell in vitro, however, the terms are used interchangeably herein without regard to whether the cells are found in vivo or in vitro.

As used herein, "dendrite" refers to the fine extensions from a neuron soma which pick up electrical and chemical impulses. The number of dendrites found on a given neuron vary extensively and depend on the specific neuron. Typical neurons may have multiple dendrites, but only a single axon, and it is the axon that migrates in response to cues to innervate a target tissue.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied.

The terms "peptide(s)", "protein(s)" and "polypeptide(s)" are used interchangeably herein.

The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence encoding a protein, or a portion thereof, or protein sequence, or portion thereof, respectively, as it normally exists in vivo.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of neural origin, e.g. neuronal cells. The term also covers so-called "leaky" promoters, which regulate expression of a selected nucleic acid primarily in one tissue, but cause expression in other tissues as well.

"Homology" and "identity" are used synonymously throughout and refer to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

A "chimeric protein" or "fusion protein" is a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The "non-human animals" of the invention include mammals such as rats, mice, rabbits, sheep, cats, dogs, cows, pigs, and non-human primates.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding a Rho family GTPase preferably includes no more than 10 kilobases (kb) of nucleic acid sequence which naturally immediately flanks the Rho family GTPase gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As used herein, "proliferating" and "proliferation" refer to cells undergoing mitosis.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the animal's system and, thus, is subject to metabolism and other like processes, for example, subcutaneous administration.

The phrase "effective amount" as used herein means that the amount of one or more agent, material, or composition comprising one or more agents as described herein which is effective for producing some desired effect in a subject; for example, an amount of the compositions described herein effective to promote neuronal regeneration, or to suppress the effects of inhibitory agents such as CSPGs amd CS-GAGs.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

(iii) Exemplary Compositions

The present invention contemplates a large number of C1 activators. C1 activators include Class I Rho family GTPases, as well as agents which promote the "on" state of Rho family GTPases. C1 activators for use in the present invention can be characterized by the ability to promote neuronal regeneration. Neuronal regeneration includes the promotion of neuronal growth and/or survival in the following scenarios: regeneration in the central and/or peripheral nervous system; in vivo and/or in vitro; following injury or in a disease state; in the presence or absence of a glial scar; in the presence or absence of inflammation.

C1 activators include Rho family GTPases such as Cdc42 (SEQ ID NO: 2), Rac1 (SEQ ID NO: 4), and RhoA (SEQ ID NO: 6). C1 activators further include variants of Rho family GTPases such as constituitively active variants of Rho family GTPases. Exemplary constituitively active Rho family GTPases which may be C1 activators include Q61L mutation in Cdc42 (SEQ ID NO:2), Q61L mutation in Rac1 (SEQ ID NO:4), Q63L mutation in RhoA (SEQ ID NO:6), G12V mutation in Cdc42 (SEQ ID NO:2), G12V mutation in Rac1 (SEQ ID NO:4), and the G14V mutation in RhoA (SEQ ID NO:6).

The present application further contemplates that GEFs, GAPs and GDIs can function as C1 activators. GEFs promote the "on" state of Rho family GTPases, and thus a nucleic acid sequence encoding a GEF polypeptide or a polypeptide comprising a GEF amino acid sequence can be a C1 activator. Additionally, agents which increase the expression or activity of a GEF may be a C1 activator. GAPs promote the "off" state of Rho family GTPases. Agents which decrease the expression or activity of a GAP may be a C1 activator. GDIs promote the "off" state of Rho family GTPases. Agents which decrease the expression or activity of a GDI may be a C1 activator.

The present invention contemplates a large number of C2 inhibitors. C2 inhibitors include variant forms of Class II Rho family GTPases, as well as agents which promote the "off" state of Rho family GTPases. C2 inhibitors for use in the present invention can be characterized by the ability to promote neuronal regeneration. Neuronal regeneration includes the promotion of neuronal growth and/or survival in the following scenarios: regeneration in the central and/or peripheral nervous system; in vivo and/or in vitro; following injury or in a disease state; in the presence or absence of a glial scar; in the presence or absence of inflammation.

C2 inhibitors include Rho family GTPases such as Cdc42 (SEQ ID NO: 2), Rac1 (SEQ ID NO: 4), and RhoA (SEQ ID NO: 6). C2 inhibitors further include variants of Rho family GTPases such as dominant negative variants of Rho family GTPases. Exemplary dominant negative Rho family GTPases which may be C1 activators include T17N mutation in Cdc42 (SEQ ID NO: 2), T17N mutation in Rac1 (SEQ ID NO: 4), and T19N mutation in RhoA (SEQ ID NO: 6). The present application further contemplates that decreasing GEF expression or activity, increasing GAP expression or activity and increasing GDI expression or activity can function as a C2 inhibitor.

Without being bound by theory, an agent identified by the subject methods as a C1 activator and/or a C2 inhibitor may function in any of a number of ways. Exemplary agents include, but are not limited to (a) nucleic acids encoding a C1 Rho family GTPase, (b) nucleic acids encoding an constitutively active (activated) C1 Rho family GTPase, (c) polypeptides comprising an amino acid sequence of a C1 Rho family GTPase, (d) polypeptides comprising an amino acid sequence of an constitutively active (activated) C1 Rho family GTPase, (e) nucleic acids encoding a dominant negative C2 Rho family GTPase, (f) polypeptides comprising an amino acid sequence of a dominant negative C2 Rho family GTPase, (g) RNAi constructs which decrease expression of a C2 Rho family GTPase, (h) antibodies which bind to and inhibit the activity (promote the "off" state) of a C2 Rho family GTPase, (i) antisense oligonucleotides which bind to and decrease the expression of a C2 Rho family GTPase, (j) small organic molecules which increaseexpression of one or more C1 Rho family GTPase, (k) small organic molecules which increase the "on" state of one or more C1 Rho family GTPase, (l) small organic molecules which decrease expression of a C2 Rho family GTPase, (m) small organic molecules which increase the "off" state of a C2 Rho family GTPase, (n) nucleic acids encoding a GTPase-activating protein (GAP) which preferentially promotes the "off" state of a C2 Rho family GTPase, (o) small organic molecules which increase expression of a GAP which preferentially promotes the "off" state of a C2 Rho family GTPase, (p) antisense oligonucleotides which decrease the expression of a GAP which preferentially promotes the "off" state of a C1 Rho family GTPase, (q) RNAi oligonucleotides or constructs which decrease the expression of a GAP which preferentially promotes the "off" state of a C1 Rho family GTPase, (r) antibodies which bind to and inhibit the activity of a GAP which preferentially promotes the "off" state of a C1 Rho family GTPase, (s) nucleic acids encoding a GEF which preferentially promotes the "on" state of a C1 Rho family GTPase, (t) small organic molecules which promote the expression of a GEF which preferentially promotes the "on" state of a C1 Rho family GTPase, (u) small organic molecules which promote the activity of a GEF which preferentially promotes the "on" state of a C1 Rho family GTPase, (v) RNAi constructs which decrease the expression of a GEF that preferentially promotes the "on" state of a C2 Rho family GTPase, (w) antisense oligonucleotides which decrease the expression of a GEF which preferentially promotes the "on" state of a C2 Rho family GTPase, (x) antisense oligonucleotides that decrease the expression of a GDI which preferentially promotes the "off" state of a C1 Rho family GTPase, (y) RNAi constructs that decrease the expression of a GDI which preferentially promotes the "off" state of a C1 Rho family GTPase, (z) small organic molecules that promote the expression or activity of a GDI which preferentially promotes the "off" state of a C2 Rho family GTPase.

The foregoing mechanisms are by no means exhaustive. Agents for use in the subject methods either promote the expression and/or "on" state of a C1 Rho family GTPase, increase the expression and/or activity of a protein which promotes the "on" state of a C1 Rho family GTPase, decrease the expression and/or activity of a protein which promotes the "off" state of a C1 Rho family GTPase, inhibit the expression and/or increase the "off" state of a C2 Rho family GTPase, increase the expression and/or activity of a protein which promotes the "off" state of a C2 Rho family GTPase, decrease the expression and/or activity of a protein which promotes the "on" state of a C2 Rho family GTPase.

In any of the foregoing, the application contemplates that C1 activators and/or C2 inhibitors may be administered alone, or may be administered in combination with one or more other agents. Similarly, in methods of screening for additional C1 activators and/or C2 inhibitors the application contemplates that agents may be screened singly or in combination with one or more other agents.

Combinations of agents include, but are not limited to (a) two or more C1 activators; (b) two or more C2 inhibitors; (c) one or more C1 activators and one or more C2 inhibitors; (d) one or more C1 activators and one or more neurotrophic factors or growth factors; (e) one or more C2 inhibitors and one or more neurotrophic factors or growth factors; (f) one or more C1 activators, one or more C2 inhibitors, and one or more neurotrophic factors or growth factors; (g) one or more C1 activators and an enzyme that digests proteoglycan sugars; (h) one or more C2 inhibitors and an enzyme that digests proteoglycan sugars; (i) one or more C1 activators, one or more C2 inhibitors, and an enzyme that digests proteoglycan sugars; (j) one or more C1 activators, one or more neurotrophic factors or growth factors, and an enzyme that digests proteoglycan sugars; (k) one or more C2 inhibitors, one or more neurotrophic factors or growth factors, and an enzyme that digests proteoglycan sugars; and (l) one or more C1 activators, one or more C2 inhibitors, one or more neurotrophic factors or growth factors, and an enzyme that digests proteoglycan sugars.

As described herein, one aspect of the invention pertains to isolated nucleic acids comprising nucleotide sequences encoding C1 activators and C2 inhibitors, and/or equivalents of such nucleic acids. Exemplary C1 activators include Cdc42, Rac1, activated (constitutively active) Cdc42, activated (constitutively active) Rac1, activated (constitutively active) RhoA, etc. Further exemplary C1 activators include nucleic acids encoding agents which promote the "on" state of a Class I Rho family GTPase. Exemplary C2 inhibitors include dominant negative Rho, dominant negative Rac1, dominant negative Cdc42, as well as nucleic acids encoding agents which promote the "off" state of a Class II Rho family GTPase. The term nucleic acid as used herein is intended to include fragments as equivalents, wherein such fragments have substantially the same function as the full length nucleic acid sequence from which it is derived. The term equivalent is understood to include nucleotide sequences encoding C1 activators and C2 inhibitors which are functionally equivalent to the C1 activators and C2 inhibitors disclosed herein, as well as C1 activators and C2 inhibitors having substantially the same function as the C1 activators and C2 inhibitors disclosed herein. Equivalent nucleotide sequences will include sequences that differ by one or more nucleotide substitutions, additions or deletions, such as allelic variants; and will, therefore, include sequences that differ from the nucleotide sequence of, for example, the wild type Cdc42 (SEQ ID NO:1), Rac1 (SEQ ID NO:3), or RhoA (SEQ ID NO:5) sequence. Equivalent sequences include those that vary from a known wild type or variant sequence due to the degeneracy of the genetic code. Equivalent sequences may also include nucleotide sequences that hybridize under stringent conditions (i.e., equivalent to about 20-27° C. below the melting temperature ($T_m$) of the DNA duplex formed in about 1 M salt) to the nucleotide sequence of a C1 activator or C2 inhibitor. Further examples of stringent hybridization conditions include a wash step of 0.2×SSC at 65° C. For the foregoing examples of equivalents to the C1 activators and C2 inhibitors for use in the methods of the present invention, one of skill in the art will recognize that an equivalent sequence retains the function of the C1 activator or C2 inhibitor. As used herein, the function of the C1 activator and/or C2 inhibitor is the ability to promote neuronal regeneration.

In one example, the invention contemplates a method of promoting neuronal regeneration by administering a C1 activator, wherein the C1 activator comprises a nucleic acid sequence which hybridizes under stringent conditions, including a wash step of 0.2×SSC at 65° C., to a nucleic acid sequence of SEQ ID NO: 1, SEQ ID NO: 3 or SEQ ID NO: 5. In another embodiment, the invention contemplates a method of promoting neuronal regeneration by administering a C2 inhibitor, wherein the C2 inhibitor comprises a nucleic acid sequence which hybridizes under stringent conditions, including a wash step of 0.2×SSC at 65° C., to a nucleic acid sequence of SEQ ID NO: 1, SEQ ID NO: 3 or SEQ ID NO: 5.

Equivalent nucleotide sequences for use in the methods described herein also include sequences which are at least 60% identical to the nucleotide sequence of a given C1 activator or C2 inhibitor. In another embodiment, the nucleotide sequence is at least 70%, 75%, 80%, 85%, 90%, 95%, 98%, 99%, or 100% identical to the nucleotide sequence of a given C1 activator or C2 inhibitor. In the foregoing, one of skill in the art will recognize that equivalent sequences at least 60%, 70%, 75%, 80%, 85%, 90%, 95%, 98%, 99%, or 100% identical to a C1 activator or C2 inhibitor, and which retain the function of the C1 activator or C2 inhibitor, are useful in the methods of the present invention. As used herein, a function of the C1 activator and/or C2 inhibitor is the ability to promote neuronal regeneration. In one embodiment, the invention contemplates a method of promoting neuronal regeneration by administering a C1 activator, wherein the C1 activator comprises a nucleic acid sequence 60%, 70%, 75%, 80%, 85%, 90%, 95%, 98%, 99% or 100% identical to the nucleic acid sequence of SEQ ID NO: 1, SEQ ID NO: 3 or SEQ ID NO: 5. In another embodiment, the invention contemplates a method of promoting neuronal regeneration by administering a C2 inhibitor, wherein the C2 inhibitor comprises a nucleic acid sequence 60%, 70%, 75%, 80%, 85%, 90%, 95%, 98%, 99% or 100% identical to the nucleic acid sequence of SEQ ID NO: 1, SEQ ID NO: 3 or SEQ ID NO: 5.

Moreover, it will be generally appreciated that, under certain circumstances, it may be advantageous to provide a variant of a C1 activator or a C2 inhibitor that functions as an antagonist (e.g, inhibits the functional activity of a C1 activator or a C2 inhibitor). In the context of the systems and methods described herein, an antagonist can be characterized by one or more of the following properties: (a) promotes the retraction of a cellular process such as an axon or dendrite, (b) decreases the rate or extent of regeneration, (c) decreases the rate or extent of regeneration in the presence of a C1 activator or a C2 inhibitor. An antagonistic variant may be useful to regulate the rate or extent of regeneration, or to prevent further neuronal growth following achievement of the desired level of regeneration.

Nucleic acids having a sequence that differs from nucleotide sequences which encode a C1 activator or C2 inhibitor due to degeneracy in the genetic code are also within the scope of the invention. Such nucleic acids encode functionally equivalent peptides but differ in sequence from wild type sequences known in the art due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence. However, it is expected that DNA sequence polymorphisms that do lead to changes in the amino acid sequences will also exist. One skilled in the art will appreciate that these variations in one or more nucleotides (up to about 3-5% of the nucleotides) of the nucleic acids encoding polypeptides having a functional activity of a C1 activator or C2 inhibitor may exist among individuals of a given species due to natural allelic variation.

In general, polypeptides referred to herein as having an activity of a C1 activator or a C2 inhibitor polypeptide (e.g., "bioactive polypeptides") are defined as polypeptides which include an amino acid sequence corresponding (e.g., at least 80%, 85%, 90%, 95%, 98%, 100% identical) to all or a portion of an amino acid sequence of a wild type C1 activator or C2 inhibitor polypeptide. Exemplary C1 activators or C2 inhibitors include wild type Rac, wild type Cdc42, wild type RhoA, activated (constitutively active) Rac, activated (constitutively active) Cdc42, activated (constitutively active) RhoA, dominant negative RhoA, dominant negative Rac1, dominant negative Cdc42, etc. Bioactive polypeptides, or bioactive fragments of said polypeptides, will have an activity of a C1 activator or C2 inhibitor. Such polypeptides promote regeneration. In one embodiment, the invention contemplates a method of promoting regeneration by administering a C1 activator, wherein the C1 activator comprises an amino acid sequence at least 80%, 85%, 90%, 95%, 98%, 99%, or 100% identical to SEQ ID NO: 2, SEQ ID NO: 4, or SEQ ID NO: 6. In another embodiment, the invention contemplates a method of promoting regeneration by administering a C2 inhibitor, wherein the C2 inhibitor comprises an amino acid sequence at least 80%, 85%, 90%, 95%, 98%, 99%, or 100% identical to SEQ ID NO: 2, SEQ ID NO: 4, or SEQ ID NO: 6.

It is further appreciated that C1 activators and C2 inhibitors for use in the methods of the invention may comprise polypeptides encoded by a nucleic acid sequence. In one embodiment, the invention contemplates a method of promoting regeneration by administering a C1 activator, wherein the C1 activator comprises an amino acid sequence encoded by a nucleic acid sequence which hybridizes under stringent conditions, including a wash step of 0.2×SSC at 65° C., to a nucleic acid sequence of SEQ ID NO: 1, SEQ ID NO: 3 or SEQ ID NO: 5. In another embodiment, the invention contemplates a method of promoting regeneration by administering a C2 inhibitor, wherein the C2 inhibitor comprises an amino acid sequence encoded by a nucleic acid sequence which hybridizes under stringent conditions, including a wash step of 0.2×SSC at 65° C., to a nucleic acid sequence of SEQ ID NO: 1, SEQ ID NO: 3 or SEQ ID NO: 5.

Moreover, it will be appreciated that, under certain circumstances, it may be advantageous to provide a polypeptide which is a variant of a C1 activator or a C2 inhibitor, and that functions as an antagonist (e.g, inhibits the function of a C1 activator or a C2 inhibitor). In the context of the systems and methods described herein, an antagonist can be characterized by one or more of the following properties: (a) promotes the retraction of a cellular process such as an axon or dendrite, (b) decreases the rate or extent of regeneration, (c) decreases the rate or extent of regeneration in the presence of a C1 activator or a C2 inhibitor. An antagonistic variant may be useful to regulate the rate or extent of regeneration, or to prevent further neuronal growth following achievement of the desired level of regeneration.

A. Classes of Inhibitors

As outlined in detail above, certain agents contemplated by the present invention exert their effect by inhibiting the expression and/or activity of a protein that endogenously functions to inhibit regeneration. The present invention contemplates methods and compositions for promoting neuronal regeneration (e.g., overcoming the inhibitory effects of a proteoglycan rich glial scar) using, for example, any of a number of inhibitory agents known in the art (e.g., antisense oligonucleotides, RNAi constructs, ribozymes, antibodies, small organic molecules, and the like). The following are illustrative examples of general methods for inhibiting the expression and/or activity of an mRNA or protein. These examples are in no way meant to be limiting, and one of skill in the art can readily select from among known methods of inhibiting expression and/or activity.

Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an -anomeric oligonucleotide. An -anomeric oligonucleotide forms specific double-stranded hybrids with complementary RNA in which, contrary to the usual-units, the strands run parallel to each other (Gautier et al., 1987, Nucl. Acids Res. 15:6625-6641). The oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

The selection of an appropriate oligonucleotide can be readily performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

In another example, it may be desirable to design an antisense oligonucleotide that binds to and mediates the degradation of more than one message. In one example, the messages may encode related protein such as isoforms or functionally redundant protein. In such a case, one of skill in the art can align the nucleic acid sequences that encode these related proteins, and design an oligonucleotide that recognizes both messages.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bemoist and Chambon, 1981, Nature 290: 304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules, or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) *Nucleic Acids Res,* 25:776-780; Wilson et al. (1994) *J Mol Recog* 7:89-98; Chen et al. (1995) *Nucleic Acids Res* 23:2661-2668; Hirschbein et al. (1997) *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAI construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Exemplary RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

Ribozymes molecules designed to catalytically cleave an mRNA transcripts can also be used to prevent translation of mRNA (See, e.g., PCT International Publication WO90/11364, published Oct. 4, 1990; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

Antibodies can be used as inhibitors of the activity of a particular protein. Antibodies can have extraordinary affinity and specificity for particular epitopes. Antibodies that bind to a particular protein in such a way that the binding of the antibody to the epitope on the protein can interfere with the function of that protein. For example, an antibody may inhibit the function of the protein by sterically hindering the proper protein-protein interactions or occupying active sites. Alternatively the binding of the antibody to an epitope on the particular protein may alter the conformation of that protein such that it is no longer able to properly function. Alternatively, the antibody may bind to a different site on the enzyme to sterically hinder the protein-protein interactions required for enzyme function. In still another example, the antibody may bind to a different site on the enzyme and alter the conformation of the enzyme such that the enzyme is no longer able to function.

Monoclonal or polyclonal antibodies can be made using standard protocols (See, for example, Antibodies: A Laboratory Manual ed. by Harlow and Lane (Cold Spring Harbor Press: 1988)). A mammal, such as a mouse, a hamster, a rat, a goat, or a rabbit can be immunized with an immunogenic form of the peptide. Techniques for conferring immunogenicity on a protein or peptide include conjugation to carriers or other techniques well known in the art.

Following immunization of an animal with an antigenic preparation of a polypeptide, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a particular polypeptide and monoclonal antibodies isolated from a culture comprising such hybridoma cells.

In the context of the present invention, antibodies can be screened and tested to identify those antibodies that can inhibit the function of a particular protein. One of skill in the art will recognize that not every antibody that is specifically immunoreactive with a particular protein will interfere with the function of that protein. However, one of skill in the art can readily test antibodies to identify those that are capable of blocking the function of a particular protein.

The term antibody as used herein is intended to include fragments thereof which are also specifically reactive with a particular polypeptide. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a particular protein conferred by at least one CDR region of the antibody.

Both monoclonal and polyclonal antibodies (Ab) directed against a particular polypeptides, and antibody fragments such as Fab, $F(ab)_2$, Fv and scFv can be used to block the action of a particular protein. Such antibodies can be used either in an experimental context to further understand the role of a particular protein in a biological process, or in a therapeutic context.

Small organic molecules can antagonize (and, in some contexts agonize) the function of a particular protein. By small organic molecule is meant a carbon contain molecule having a molecular weight less than 2500 amu, more preferably less than 1500 amu, and even more preferably less than 750 amu.

Small organic molecules can be readily identified by screening libraries of organic molecules and/or chemical compounds to identify those compounds that have a desired function. Without being bound by theory, small organic molecules may exert their inhibitory function in any of a number of ways. In addition to screening readily available libraries to identify small organic molecules with a particular inhibitory function, the present invention contemplates the rational design and testing of small organic molecules that can inhibit the function of a particular enzyme. For example, based on molecular modeling of the binding site of a particular enzyme, one of skill in the art can design small molecules that can occupy that binding pocket. Such small organic molecules would be candidate inhibitors of the function of the particular enzyme.

The present invention contemplates a large number of agents that function as inhibitors including nucleic acid, peptide, polypeptide, small organic molecule, antisense oligonucleotide, RNAi construct, antibody, ribozyme, and mimetic based agents that function as inhibitors.

(iv) Methods of Expressing C1 Activators and C2 Inhibitors for Use in the Subject Methods The systems and methods described herein also provide expression vectors containing a nucleic acid encoding a Class I Rho family GTPase, a nucleic acid encoding an activated (constitutively active) Class I Rho family GTPase, a nucleic acid encoding a dominant negative Class II Rho family GTPase, a nucleic acid encoding an agent which promotes the "on" state of a Class I Rho family GTPase, or a nucleic acid encoding an agent which increases the "off" state of a Class II Rho family GTPase, operably linked to at least one transcriptional regulatory sequence. Regulatory sequences are art-recognized and are selected to direct expression of the subject proteins. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences may be used in these vectors to express nucleic acid sequences encoding the agents of this invention. Such useful expression control sequences, include, for example, a viral LTR, such as the LTR of the Moloney murine leukemia virus, the LTR of the Herpes Simplex virus-1, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

Moreover, the gene constructs can be used to deliver nucleic acids encoding the subject polypeptides. Thus, another aspect of the invention features expression vectors for in vivo or in vitro transfection, viral infection and expression of a subject polypeptide in particular cell types.

Expression constructs of the subject agents may be administered in biologically effective carriers, e.g. any formulation or composition capable of effectively delivering the recombinant gene to cells in vivo or in vitro. Approaches include insertion of the subject gene in viral vectors including recombinant retroviruses, adenovirus, adeno-associated virus, herpes simplex virus-1, lentivirus, mammalian baculovirus or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct, electroporation or $CaPO_4$ precipitation. One of skill in the art can readily select from available vectors and methods of delivery in order to optimize expression in a particular cell type or under particular conditions.

Retrovirus vectors and adeno-associated virus vectors have been frequently used for the transfer of exogenous genes. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes. Thus, recombinant retrovirus can be constructed in which part of the retroviral coding sequence (gag, pol, env) has been replaced by nucleic acid encoding one of the subject proteins rendering the retrovirus replication defective. The replication defective retrovirus is then packaged into virions through the use of a helper virus by standard techniques which can be used to infect a target cell. Protocols for producing recombinant retroviruses and for infecting cells in vitro or in vivo with such viruses can be found in *Current Protocols in Molecular Biology*, Ausubel, F. M. et al. (eds.) Greene Publishing Associates, (2000), and other standard laboratory manuals. Examples of suitable retroviruses include pBPSTR1, pLJ, pZIP, pWE and pEM which are known to those skilled in the art. Examples of suitable packaging virus lines for preparing both ecotropic and amphotropic retroviral systems include ψCrip, ψCre, ψ2, ψAm, and PA317.

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein; or coupling cell surface receptor ligands to the viral env proteins. Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector into an amphotropic vector.

Moreover, use of retroviral gene delivery can be further enhanced by the use of tissue- or cell-specific transcriptional regulatory sequences which control expression of the gene of the retroviral vector such as tetracycline repression or activation.

Another viral gene delivery system which has been employed utilizes adenovirus-derived vectors. The genome of an adenovirus can be manipulated so that it encodes and expresses a gene product of interest but is inactivated in terms of its ability to replicate in a normal lytic viral life cycle. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they can be used to infect a wide variety of cell types, including airway epithelium, endothelial cells, hepatocytes, and muscle cells. Furthermore, the virus particle is relatively stable and amenable to purification and concentration, and as above, can be modified so as to affect the spectrum of infectivity.

Yet another viral vector system is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158: 97-129). It is also one of the few viruses that may integrate its DNA into non-dividing cells, and exhibits a high frequency of stable integration.

Another viral delivery system is based on herpes simplex-1 (HSV-1). HSV-1 based vectors may be especially useful in the methods of the present invention because they have been previously shown to infect neuronal cells. Given that many adult neuronal cells are post-mitotic, and thus have been difficult to infect using some other commonly employed viruses, the use of HSV-1 represents a substantial advance and further underscores the potential utility of viral based systems to facilitate gene expression in the nervous system (Agudo et al. (2002) *Human Gene Therapy* 13: 665-674; Latchman (2001) *Neuroscientist* 7: 528-537; Goss et al. (2002) *Diabetes* 51: 2227-2232; Glorioso (2002) *Current Opin Drug Discov Devel* 5: 289-295; Evans (2002) *Clin Infect Dis* 35: 597-605; Whitley (2002) *Journal of Clinical Invest* 110: 145-151; Lilley (2001) *Curr Gene Ther* 1: 339-359).

The above cited examples of viral vectors are by no means exhaustive. However, they are provided to indicate that one of skill in the art may select from well known viral vectors, and select a suitable vector for expressing a particular protein in a particular cell type.

In addition to viral transfer methods, such as those illustrated above, non-viral methods can be used to express a subject polypeptide. Many nonviral methods of gene transfer rely on normal mechanisms used by cells for the uptake and intracellular transport of macromolecules. Exemplary gene delivery systems of this type include liposomal derived systems, poly-lysine conjugates, and artificial viral envelopes.

It may sometimes be desirable to introduce a nucleic acid directly to a cell, for example a cell in culture or a cell in an animal. Such administration can be done by injection of the nucleic acid (e.g., DNA, RNA) directly at the desired site. Such methods are commonly used in the vaccine field, specifically for administration of "DNA vaccines", and include condensed DNA (U.S. Pat. No. 6,281,005).

In addition to administration of nucleic acids, the systems and methods described herein contemplate that polypeptides may be administered directly. Some proteins, for example factors that act extracellularly by contacting a cell surface receptor, such as growth factors, may be administered by simply contacting cells with said protein. For example, cells are typically cultured in media which is supplemented by a number of proteins such as FGF, TGFβ, insulin, etc. These proteins influence cells by simply contacting the cells. The current invention contemplates that some C1 activators and/or C2 inhibitors can act by simply contacting cells. Such a method similarly pertains to other agents such as small organic molecules and chemical compounds. These agents may either exert their effect at the cell surface, or may be able to permeate the cell membrane without the need for additional manipulation.

In another embodiment, a C1 activator or C2 inhibitor polypeptide is directly introduced into a cell. Methods of directly introducing a polypeptide into a cell include, but are not limited to, protein transduction and protein therapy. For example, a protein transduction domain (PTD) can be fused to a nucleic acid encoding a C1 activator or a C2 inhibitor, and the fusion protein is expressed and purified. Fusion proteins containing the PTD are permeable to the cell membrane, and thus cells can be directly contacted with a fusion protein (Derossi et al. (1994) *Journal of Biological Chemistry* 269: 10444-10450; Han et al. (2000) *Molecules and Cells* 6: 728-732; Hall et al. (1996) *Current Biology* 6: 580-587; Theodore et al. (1995) *Journal of Neuroscience* 15: 7158-7167).

Although some protein transduction based methods rely on fusion of a polypeptide of interest to a sequence which mediates introduction of the protein into a cell, other protein transduction methods do not require covalent linkage of a protein of interest to a transduction domain. A least two commercially available reagents exist that mediate protein transduction without covalent modification of the protein (CHARIOT, produced by Active Motif, BIOPORTER Protein Delivery Reagent, produced by Gene Therapy Systems).

Briefly, these protein transduction reagents can be used to deliver proteins, peptides and antibodies directly to cells including mammalian cells. Delivery of proteins directly to cells has a number of advantages. Firstly, many current techniques of gene delivery are based on delivery of a nucleic acid sequence which must be transcribed and/or translated by a cell before expression of the protein is achieved. This results in a time lag between delivery of the nucleic acid and expression of the protein. Direct delivery of a protein decreases this delay. Secondly, delivery of a protein often results in transient expression of the protein in a cell.

As outlined herein, protein transduction mediated by covalent attachment of a PTD to a protein can be used to deliver a protein to a cell. These methods require that individual proteins be covalently appended with PTD moieties. In contrast, methods such as CHARIOT and BIOPORTER facilitate transduction by forming a noncovalent interaction between the reagent and the protein. Without being bound by theory, these reagents are thought to facilitate transit of the cell membrane, and following internalization into a cell the reagent and protein complex disassociates so that the protein is free to function in the cell.

In another aspect, this application includes recombinant forms of the subject C1 activators and C2 inhibitors. Recombinant polypeptides preferred by the present invention, in addition to native wild type Rho family GTPases and known constitutively active and dominant negative Rho family GTPases, are at least 60% identical, more preferably 70% identical and most preferably 80% identical with an amino acid sequence of a wild type C1 activator or C2 inhibitor. Additional preferred recombinant polypeptides comprise an amino acid sequence at least 85%, 90%, 95%, 98%, or 100% identical to an amino acid sequence of a wild type C1 activator or C2 inhibitor. The invention further concerns polypeptides comprising an amino acid sequence at least 80%, 85%, 90%, 95%, 98% or 100% identical to a bioactive fragment of a wild type C1 activator or C2 inhibitor. Any of the foregoing polypeptides comprising all or a bioactive portion of a wild type C1 activator or C2 inhibitor may be characterized by an activity of a C1 activator or C2 inhibitor: the ability to promote neuronal regeneration.

In one example, the application provides a method of promoting neuronal regeneration, comprising administering a C1 activator wherein the C1 activator comprises an amino acid sequence at least 60%, 70%, 80%, 85%, 90%, 95%, 98%, 99%, or 100% identical to SEQ ID NO: 2, SEQ ID NO: 4 or SEQ ID NO: 6. In another embodiment, the application provides a method of promoting neuronal regeneration, comprising administering a C2 inhibitor wherein the C2 inhibitor comprises an amino acid sequence at least 60%, 70%, 80%, 85%, 90%, 95%, 98%, 99%, or 100% identical to SEQ ID NO: 2, SEQ ID NO: 4 or SEQ ID NO: 6.

This application also describes methods for producing the subject polypeptides. For example, a host cell transfected with a nucleic acid vector directing expression of a nucleotide sequence encoding the subject polypeptides can be cultured under appropriate conditions to allow expression of the peptide to occur. The polypeptide may be secreted and isolated from a mixture of cells and medium containing the recombinant polypeptide. Alternatively, the peptide may be expressed cytoplasmically and the cells harvested, lysed and the protein isolated. A cell culture includes host cells, media and other by-products. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In one example, the recombinant polypeptide is a fusion protein containing a domain which facilitates its purification, such as a GST fusion protein. In another example, the subject recombinant polypeptide may include one or more additional domains which facilitate immunodetection, purification, and the like. Exemplary domains include HA, FLAG, GST, His, and the like.

Further exemplary domains include a protein transduction domain (PTD) which facilitates the uptake of proteins by cells.

This application also describes a host cell which expresses a recombinant form of the subject polypeptides. The host cell may be a prokaryotic or eukaryotic cell. Thus, a nucleotide sequence derived from the cloning of a protein encoding all or a selected portion (either an antagonistic portion or a bioactive fragment) of the full-length protein, can be used to produce a recombinant form of a polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant polypeptides by microbial means or tissue-culture technology in accord with the subject invention. Such methods are used to produce experimentally useful proteins that include all or a portion of the subject nucleic acids. For example, such methods are used to produce fusion proteins including domains which facilitate purification or immunodetection, and to produce recombinant mutant forms of a protein (for example a dominant negative or activated (constitutively active) form of a Rho family GTPase).

The recombinant genes can be produced by ligating a nucleic acid encoding a protein, or a portion thereof, into a vector suitable for expression in either prokaryotic cells, eukaryotic cells, or both. Expression vectors for production of recombinant forms of the subject polypeptides include plasmids and other vectors. For instance, suitable vectors for the expression of a polypeptide include plasmids of the types: pBR322-derived plasmids, pEMBL-derived plasmids, pEX-derived plasmids, pGEX-derived plasmids, pTrc-His-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae.

Many mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo, pBacMam-2, and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. For other suitable expression systems for both prokaryotic and eukaryotic cells, as well as general recombinant procedures, see *Molecular Cloning A Laboratory Manual,* 3rd Ed., ed. by Sambrook and Russell (Cold Spring Harbor Laboratory Press: 2001).

In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a protein, such as a form lacking a portion of the N-terminus, e.g. a truncation mutant, it may be necessary to add a start codon (ATG) to the oligonucleotide fragment containing the desired sequence to be expressed. It is well known in the art that a methionine at the N-terminal position can be enzymatically cleaved by the enzyme methionine aminopeptidase (MAP).

Techniques for making fusion genes are known to those skilled in the art. The joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another example, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence.

The present invention also makes available isolated polypeptides which are isolated from, or otherwise substantially free of other cellular and extracellular proteins. The term "substantially free of other cellular or extracellular proteins" (also referred to herein as "contaminating proteins") or "substantially pure or purified preparations" are defined as encompassing preparations having less than 20% (by dry weight) contaminating protein, and preferably having less than 5% contaminating protein. Functional forms of the subject C1 activators or C2 inhibitors can be prepared as purified preparations by using a cloned gene as described herein. By "purified", it is meant, when referring to peptide or nucleic acid sequences, that the indicated molecule is present in the substantial absence of other biological macromolecules, such as other proteins. The term "purified" as used herein preferably means at least 80% by dry weight, more preferably in the range of 95-99% by weight, and most preferably at least 99.8% by weight, of biological macromolecules of the same type present (but water and buffers can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

Isolated peptidyl portions of proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry.

The recombinant polypeptides of the present invention also include versions of those proteins that are resistant to proteolytic cleavage. Variants of the present invention also include proteins which have been post-translationally modified in a manner different than the authentic protein. Modification of the structure of the subject polypeptides can be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the polypeptides described in more detail herein. Such modified peptides can be produced, for instance, by amino acid substitution, deletion, or addition.

For example, it is reasonable to expect that, in some instances, an isolated replacement of a leucine with an isoleucine or valine, an aspartate with a glutamate, a threonine with a serine, or a similar replacement of an amino acid with a structurally related amino acid (e.g., isosteric and/or isoelectric mutations) may not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamate, cysteine, serine, threonine, tyrosine. Phenylalanine, tryptophan, and tyrosine a re sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 5th ed. by Berg, Tymoczko and Stryer, WH Freeman and Co.: 2002). Whether a change in the amino acid sequence of a peptide results in a functional variant (e.g. functional in the sense that it acts to mimic or antagonize the wild type form) can be determined by assessing the ability of the variant peptide to produce a response in cells in a fashion similar to the wild type protein, or competitively inhibit such a response. Polypeptides in which more than one replacement has taken place can readily be tested in the same manner.

Advances in the fields of combinatorial chemistry and combinatorial mutagenesis have facilitated the making of polypeptide variants (Wissmanm et al. (1991) *Genetics* 128: 225-232; Graham et al. (1993) *Biochemistry* 32: 6250-6258; York et al. (1991) *Journal of Biological Chemistry* 266: 8495-8500; Reidhaar-Olson et al. (1988) *Science* 241: 53-57). Given one or more assays for testing polypeptide variants, one can assess whether a given variant functions as a C1 activator or C2 inhibitor, or whether a given variant has an antagonistic function. In the context of the present invention, several methods for assaying the functional activity of potential C1 activators or C2 inhibitors are provided. Activity can be accessed in vitro, for example, in the culture systems provided in the examples. Furthermore, the function of a polypeptide variant can be examined in primary neural cultures, fibroblasts, and other cells and cell lines in vitro. Given the well appreciated role of Rho family GTPases generally in the extension of cellular processes from neural as well as fibroblastic cell types, one of skill in the art will recognize that such cells and cell lines provide an assay for characterizing the function of a variant polypeptide which may function as a C1 activator or C2 inhibitor.

To further illustrate, the invention contemplates a method for generating sets of combinatorial mutants of C1 activators and C 2 inhibitors as well as truncation mutants, and is especially useful for identifying potential variant sequences that maintain at least one function (activity) of a C1 activator or C2 inhibitor. Such a method is similarly useful for identifying potential variant sequences that antagonize the function of a wild type C1 activator or C2 inhibitor. The purpose of screening such combinatorial libraries is to generate, for example, novel variants which can act as either agonists or antagonists, or alternatively, possess novel activities all together.

In one aspect of this method, the amino acid sequences for a population of Class I Rho family GTPase proteins, Class II Rho family GTPase proteins, Class I activators, or Class II inhibitors are aligned, preferably to promote the highest homology possible. By a population of proteins is meant the alignment of, for example, Class I Rho family GTPase proteins from several different species (e.g., human, mouse, rat, etc.). Amino acids which appear at each position of the aligned sequences are selected to create a degenerate set of combinatorial sequences. In one example, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g. for phage display) containing the set of sequences therein.

The library of potential variants can be generated from a degenerate oligonucleotide sequence using a variety of methods. Chemical synthesis of a degenerate gene sequence can be carried out in an automatic DNA synthesizer, and the synthetic genes then ligated into an appropriate expression vector. One purpose of a degenerate set of genes is to provide, in one mixture, all the sequences encoding the desired set of potential variant sequences. The synthesis of degenerate oligonucleotides is known in the art.

A range of techniques are known for screening gene products of combinatorial libraries made by point mutations, and for screening cDNA libraries for gene products having a certain property. Such techniques will be generally adaptable for rapid screening of the gene libraries generated by the combinatorial mutagenesis of Class I Rho family GTPases, Class II Rho family GTPases, Class I activators, or Class II inhibitors. These techniques are also applicable for rapid screening of other gene libraries. One example of the techniques used for screening large gene libraries includes cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

The application also describes reducing a protein to generate mimetics, e.g. peptide or non-peptide agents. Such mimetics may either possess a functional activity of a Class I activator or Class II inhibitor (e.g., promote neuronal regeneration) or such mimetics may function as an antagonist. Mimetics that are either bioactive in the subject methods or function antagonistically may be readily tested using any in vitro method known in the art and outlined in detail herein. Similarly mimetics having the desired activity (e.g., bioactive or antagonistic) can be selected by testing a given mimetic in vivo and assessing whether said mimetic promotes neuronal regeneration.

(v) In Vitro Models of Neuronal Regeneration

Given the importance of the development of methods to promote neuronal regeneration, there exists a need for improved in vitro assays in which agents can be studied and or screened for the ability to promote neuronal regeneration. The present application provides two novel models which can be used to examine neuronal regeneration in vitro. These models c an also be used to identify a gents which promote neuronal regeneration.

One model is a three dimensional agarose gel described in detail in Examples 1 and 2. Briefly, the growth and survival of neuronal cells can be measured in this three dimensional gel. For example, cell can be cultured in a layer containing only agarose, and the ability of the cells to extend cellular processes into an opposing layer of agarose which contains an inhibitory substance can be measured. The inhibitory substance can be chondroitin sulfate GAGs, CSPGs, or another inhibitory substance. Examples of other inhibitory substances include proteoglycans and extracellular matrix proteins commonly found in glial scars. Further examples of inhibitory substances include factors which are up-regulated as part of the inflammatory response. In this way, the three dimensional agarose gel can be used to mimic neuronal regeneration in the presence of a glial scar. Agents can be added to the layer containing the inhibitory substance, or agents can be added to the neuronal cells themselves, and neuronal growth, survival and behavior can be readily assessed in the presence or absence of a given agent. An agent which increases the ability of neurons to extend processes into the layer which includes an inhibitory substance, such as chondroitin sulfate (CSPGs or CS-GAGs), is an agent which may promote neuronal regeneration.

A second model is the two dimensional coverslip model described in Examples 4 and 5. Briefly, the growth and survival of neuronal cells can be measured in this two dimensional model. Coverslips are coated to create alternating lanes which are either permissive or inhibitory for neuronal growth. For example, alternating lanes of chondroitin sulfate GAGs are fixed to the surface of the coverslip. The ability of cells plated on the coverslip to extend processes along the short axis of the coverslip (from a permissive zone into an inhibitory zone) can be measured. Agents can be administered to the cells themselves, or agents can administered to the surface of the coverslip, and neuronal growth, survival and behavior can be readily assessed in the presence or absence of a given agent. An agent which increases the ability of neurons to extend processes along the short axis of the coverslip (from a permissive zone into an inhibitory zone) is an agent which may promote neuronal regeneration.

(vi) Method of Screening

This application describes methods of promoting regeneration by promoting the "on" state of Class I Rho family GTPases or promoting the "off" state of of Class II Rho family GTPases. With the importance of providing effective methods and compositions for promoting neuronal regeneration in mind, the present invention contemplates methods of identifying agents which are activated or promote the "on" statea Class I Rho family GTPase and/or inhibit (promote the "off" state) a Class II Rho family GTPase (e.g, C1 activators and/or C2 inhibitors). Exemplary agents can promote neuronal regeneration when administered in an effective amount.

As described in detail herein, agents which can antagonize the activity of a Class I activator and/or Class II inhibitor also have substantial utility. Such antagonists may be used to limit the rate or extent of neuronal regeneration, or to otherwise modulate the activity of a C1 activator and/or C2 inhibitor. Accordingly, the present invention further contemplates methods of identifying agents which antagonize the activity of a C1 activator and/or C2 inhibitor. Exemplary agents can modulate the rate and/or extent of neuronal regeneration when administered in an effective amount.

Agents screened (e.g., a single agent, a combination of two or more agents, a library of agents) include nucleic acids, peptides, proteins, antibodies, antisense RNAs, RNAi constructs (including siRNAs), chemical compounds, and small organic molecules. Agents may be screened individually, in combination, or as a library of agents.

Without being bound by theory, an agent identified by the subject methods as a C1 activator and/or a C2 inhibitor may function in any of a number of way. Exemplary agents include (a) nucleic acids encoding a C1 Rho family GTPase, (b) nucleic acids encoding an activated (constitutively active) C1 Rho family GTPase, (c) polypeptides comprising an amino acid sequence of a C1 Rho family GTPase, (d) polypeptides comprising an amino acid sequence of an activated (constitutively active) C1 Rho family GTPase, (e) nucleic acids encoding a dominant negative C2 Rho family GTPase, (f) polypeptides comprising an amino acid sequence of a dominant negative C2 Rho family GTPase, (g) RNAi constructs which decrease expression of a C2 Rho family GTPase, (h) antibodies which bind to and inhibit the activity (promote the "off" state) of a C2 Rho family GTPase, (i) antisense oligonucleotide which bind to and decrease the expression of a C2 Rho family GTPase, (j) small organic molecules which increase expression of one or more C1 Rho family GTPase, (k) small organic molecules which promote the "on" state of one or more C1 Rho family GTPase, (l) small organic molecules which decrease expression of a C2 Rho family GTPase, (m) small organic molecules which promote the "off" state of a C2 Rho family GTPase, (n) nucleic acids encoding a GTPase-activating protein (GAP) which preferentially inhibits the activity (promote the "off" state) of a C2 Rho family GTPase, (o) small organic molecules which increase expression of a GAP which preferentially inhibits the activity (promote the "off" state) of a C2 Rho family GTPase, (p) antisense oligonucleotides which decrease the expression of a GAP which preferentially inhibits the activity (promote the "off" state) of a C1 Rho family GTPase, (q) RNAi constructs which decrease the expression of a GAP which preferentially inhibits the activity (promote the "off" state) of a C1 Rho family GTPase, (r) antibodies which bind to and inhibit the activity (promote the "off" state) of a GAP which preferentially inhibits the activity of a C1 Rho family GTPase, (s) nucleic acids encoding a GEF which preferentially promotes the "on" state of a C1 Rho family GTPase, (t) small organic molecules which promote the expression of a GEF which preferentially promotes the "on" state of a C1 Rho family GTPase, (u) small organic molecules which promote the activity of a GEF which preferentially promotes the "on" state of a C1 Rho family GTPase, (v) RNAi constructs which decrease the expression of a GEF that preferentially promotes the "on" state of a C2 Rho family GTPase, (w) antisense oligonucleotides which decrease the expression of a GEF which preferentially promotes the "on" state of a C2 Rho family GTPase, (x) antisense oligonucleotides that decrease the expression of a GDI which preferentially promotes the "off" state of a C1 Rho family GTPase, (y) RNAi constructs that decrease the expression of a GDI which preferentially promotes the "off" state of a C1 Rho family GTPase, (z) small organic molecules that promote the expression or activity of a GDI which preferentially promotes the "off" state of a C2 inhibitor. The foregoing mechanisms are by no means exhaustive. Agents for use in the subject methods either promote the expression and/or activity of a C1 Rho family GTPase, increase the expression and/or activity of a protein which promotes the "on" state of a C1 Rho family GTPase, decrease the expression and/or activity of a protein which promotes the "off" state of a C1 Rho family GTPase, inhibit the expression and/or activity of a C2 Rho family GTPase, increase the expression and/or activity of a protein which promotes the "off" state of a C2 Rho family GTPase, decrease the expression and/or activity of a protein which promotes the "on" state of a C2 Rho family GTPase.

Similarly, and without being bound by theory, exemplary antagonists identified by the subject methods may function in any of a number of way. Exemplary agents include (a) nucleic acids encoding a C2 Rho family GTPase, (b) nucleic acids encoding an activated (constitutively active) C2 Rho family GTPase, (c) polypeptides comprising an amino acid sequence of a C2 Rho family GTPase, (d) polypeptides comprising an amino acid sequence of an activated (constitutively active) C2 Rho family GTPase, (e) nucleic acids encoding a dominant negative C1 Rho family GTPase, (f) polypeptides comprising an amino acid sequence of a dominant negative C1 Rho family GTPase, (g) RNAi constructs which decrease expression of a C1 Rho family GTPase, (h) antibodies which bind to and inhibit the activity (promote the "off" state) of a C1 Rho family GTPase, (i) antisense oligonucleotide which bind to and decrease the expression of a C1 Rho family GTPase, (j) small organic molecules which increase expression of one or more C2 Rho family GTPase, (k) small organic molecules which increase the activity (promote the "on" state) of one or more C2 Rho family GTPase, (l) small organic molecules which decrease expression of a C1 Rho family GTPase, (m) small organic molecules which decrease activity (promote the "off" state) of a C1 Rho family GTPase, (n) nucleic acids encoding a GTPase-activating protein (GAP) which preferentially inhibits the activity (promote the "off" state) of a C1 Rho family GTPase, (o) small organic molecules which increase expression of a GAP which preferentially inhibits the activity of a C1 Rho family GTPase, (p) antisense oligonucleotides which decrease the expression of a GAP which preferentially inhibits the activity (promote the "off" state) of a C2 Rho family GTPase, (q) RNAi constructs which decrease the expression of a GAP which preferentially inhibits the activity (promote the "off" state) of a C2 Rho family GTPase, (r) antibodies which bind to and inhibit the activity of a GAP which preferentially inhibits the activity (promote the "off" state) of a C2 Rho family GTPase, (s) nucleic acids encoding a GEF which preferentially promotes the "on" state of a C2 Rho family GTPase, (t) small organic molecules which promote the expression of a GEF which preferentially promotes the "on" state of a C2 Rho family GTPase, (u) small organic molecules which promote the activity of a GEF which preferentially promotes the "on" state of a C2 Rho family GTPase, (v) RNAi constructs which decrease the expression of a GEF that preferentially promotes the "on" state of a C1 Rho family GTPase, (w) antisense oligonucleotides which decrease the expression of a GEF which preferentially promotes the "on" state of a C1 Rho family GTPase, (x) antisense oligonucleotides that decrease the expression of a GDI which preferentially promotes the "off" state of a C2 Rho family GTPase, (y) RNAi constructs that decrease the expression of a GDI which preferentially promotes the "off" state of a C2 Rho family GTPase, (z) small organic molecules that promote the expression or activity of a GDI which preferentially promotes the "on" state of a C1 inhibitor. The foregoing mechanisms are by no means exhaustive. Antagonists for use in the subject methods either promote the expression and/or activity of a C2 Rho family GTPase, increase the expression and/or activity of a protein which promotes the "on" state of a C2 Rho family GTPase, decrease the expression and/or activity of a protein which promotes the "off" state of a C2 Rho family G TPase, inhibit the expression and/or activity of a C1 Rho family GTPase, increase the expression and/or activity of a protein which promotes the "off" state of a C1 Rho family GTPase, decrease the expression and/or activity of a protein which promotes the "off" state of a C1 Rho family GTPase.

In many drug screening programs that test libraries of nucleic acids, polypeptides, chemical compounds and natural extracts, high throughput assays are desirable to increase the number of agents surveyed in a given period of time. Assays that are performed in cell-free systems, such as may be derived with purified or semi-purified proteins, are often preferred as "primary" screens in that they can be generated to permit rapid development and relatively easy detection of an alteration in a molecular target which is mediated by a test agent. Cell free systems include in vitro systems (preparations of proteins and agents combined in a test tube, Petri dish, etc.), as well as cell free systems such as those prepared from egg extracts or reticulocyte lysates. Moreover, the effects of cellular toxicity and/or bioavailability of the test agents can be generally ignored in such a system, the assay instead being focused primarily on the effect of the agent.

A primary screen can be used to narrow down agents that are more likely to have an effect on neuronal regeneration, in vitro and/or in vivo. Such a cell free system for use in the present invention may include a biochemical assay measuring activity of a Rho family GTPase. For example, a Class I Rho family GTPase may be exposedwith one or more agents (e.g., individual candidate agents, combinations of two or more agents, a library of nucleic acids, polypeptides, small organic molecules, chemical compounds, etc.) and the ability of the a gent to promote the "on" state of the Class I Rho family GTPase can be measured. One or more agents that promote the "on" state of a Class I Rho family GTPase are candidate agents for use in the subject methods of promoting neuronal regeneration. In another example, a Class II Rho family GTPase may be exposed with one or more agents (e.g., individual candidate agents, combinations of two or more agents, a library of nucleic acids, polypeptides, small organic molecules, chemical compounds, etc.) and the ability of the agent to promote the "off" state of the Class II Rho family GTPase can be measured. One or more agents which promotes the "off" state of a Class II Rho family GTPase are candidate agents for use in the subject methods of promoting neuronal regeneration.

The efficacy of the agent can be assessed by generating dose response curves from data obtained using various concentrations of the test agent. Moreover, a control assay can also be performed to provide a baseline for comparison. Such candidates can be further tested for efficacy in promoting extension of cellular processes in neuronal and/or fibroblastic cells in vitro, for efficacy in neuronal regeneration in vitro or in vivo, and for efficacy in promoting neurite extension through a glial scar in vitro or in in vivo.

In the foregoing screening methods, the application further contemplates that screening assays may be performed to identify agents that antagonize the activity of a Rho family GTPase. For example, a Class I Rho family GTPase may be contacted with one or more agents (e.g., individual candidate agents, combinations of two or more agents, a library of nucleic acids, polypeptides, small organic molecules, chemical compounds, etc.) and the ability of the agent to promote the "off" state of the Class I Rho family GTPase can be measured. One or more agents which promotes the "off" state of a Class I Rho family GTPase are candidate antagonists for use in inhibiting neuronal regeneration, limiting the rate and/or extent of neuronal regeneration, or antagonizing the activity of a C1 activator and/or a C2 inhibitor. In another example, a Class II Rho family GTPase may be exposed with one or more agents (e.g., individual candidate agents, combinations of two or more agents, a library of nucleic acids, polypeptides, small organic molecules, chemical compounds, etc.) and the ability of the agent to promote the "on" state of the Class II Rho family GTPase can be measured. One or more agents that promotes the "on" state of a Class II Rho family GTPase are candidate antagonists for use in inhibiting neuronal regeneration, limiting the rate and/or extent of neuronal regeneration, or antagonizing the activity of a C1 activator and/or a C2 inhibitor.

In the foregoing screening methods, the invention further contemplates that screening assays may be performed to identify agents which promote or antagonize the "on" or "off" state of a Rho family GTPase, wherein the Rho family GTPase is either a wild type Rho family GTPase, an activated variant of a Rho family GTPase, a dominant negative variant of a Rho family GTPase, or a variant Rho family GTPase. In one embodiment, the method comprises identifying agents which promote the "on" or "off" state of a Rho family GTPase, wherein the Rho family GTPase comprises an amino acid sequence at least 80%, 85%, 90%, 95%, 98%, 99%, or 100% identical to SEQ ID NO: 2, SEQ ID NO: 4 or SEQ ID NO: 6. In another embodiment, the method comprises identifying agents which antagonize the "on" or "off" state of a Rho family GTPase, wherein the Rho family GTPase comprises an amino acid sequence at least 80%, 85%, 90%, 95%, 98%, 99%, or 100% identical to SEQ ID NO: 2, SEQ ID NO: 4 or SEQ ID NO: 6.

In addition to cell-free assays, such as described above, the invention further contemplates the generation of cell-based assays for identifying agents that modulate (increase or decrease) the "on" or "off" state of a Rho family GTPase. Cell-based assays may be performed as either a primary screen, or as a secondary screen to confirm the activity of agents identified in a cell free screen, as outlined in detail above. Such cell based assays can employ any cell-type. Exemplary cell types include neuronal cell lines, primary neural cultures, fibroblasts, lymphocytes, mesenchymal cells, etc. Cells in culture are exposed with one or more agents, and the ability of the one or more agents to promote the extension of cellular processes (in the case of C1 activates and/or C2 inhibitors) is measured. Agents which promote the extension of cellular processes are candidate agents for use in the subject methods of promoting neuronal regeneration.

One class of agents that may promote the activity of a Rho family GTPase (e.g., promote the "on" state of a Class I Rho family GTPase, inhibit the "off" state of a Class I Rho family GTPase, promote the "off" state of a Class II Rho family GTPase, and/or inhibit the "on" state of a Class II Rho family GTPase) are agents which bind directly to a Class I or Class II Rho family GTPase. Similarly, one class of agents which antagonize the activity of a Rho family GTPase (e.g., promote the "off" state of a Class I Rho family GTPase, inhibit the "on" state of a Class I Rho family GTPase, promote the "on" state of a Class II Rho family GTPase, and/or inhibit the "off" state of a Class II Rho family GTPase) are agents which bind directly to a Class I or Class II Rho family GTPase. Accordingly, the present invention contemplates screening for agents which bind to, either directly or indirectly, a Rho family GTPase. Many methods exist in the art for assessing protein-protein, protein-nucleic acid, protein-antibody, and protein-small molecule interactions. Exemplary methods include two-hybrid screens, affinity chromatography, immunoprecipitation, and the like. One of skill in the art can select commonly used methods for detecting the interaction of a Class I or Class II Rho family GTPase with an agent including proteins, nucleic acids, small molecule, chemical compounds, antibodies, etc.

In addition to the cell free and cell based assays described above. Agents may be screened using either of the novel three dimensional or two dimensional assay systems outlined in detail in section (v) and in the examples.

(vii) Methods of Administration of Nucleic Acids, Proteins, Chemical Compounds and Pharmaceutical Compositions of Agents An agent identified by the subject methods has many potential uses. Such an agent may be a nucleic acid, peptide, polypeptide, RNAi construct, chemical compound, small organic molecule, antisense RNA, antibody, and the like. By agent is meant to include a single agent, or a combination of agents which together possess the desired activity. An agent may either increase or decrease the "on" or "off" state of a Rho family GTPase and modulate neuronal regeneration. In one embodiment, an agent promotes neuronal regeneration and promotes the "on" state of a Class I Rho family GTPase and/or promotes the "off" state of a Class II Rho family GTPase. In another embodiment, an agent limits the rate and/or extent of neuronal regeneration and inhibits the "on" state of a Class I Rho family GTPase and/or promotes the "off" state of a Class II Rho family GTPase.

Agents that are C1 activators and/or C2 inhibitors may be useful in a therapeutic context. For example, glial scarring which occurs following an injury to the central nervous system inhibits neuronal regeneration. This phenomenon is thought to account for the minimal regeneration observed in the CNS following injury. Furthermore, this phenomenon is though to account for the minimal improvement which occurs following onset of symptoms of a neurodegenerative disease. In addition to glial scarring, other injury or disease to the central or peripheral nervous system can impair the ability of the damaged neuronal tissue to regenerate following the injury. Impairment of regeneration in the central or peripheral nervous system may be due, for example, to inflammation, to a physical and/or molecular barrier which prevents regeneration, or to cellular damage which prevents neuronal cells from responding to local molecular, chemical and/or electrical cues. Accordingly, agents which promote regeneration of either neuronal cells in the central nervous system or neuronal cells in the peripheral nervous system represent an important therapeutic method to improve recovery from injury, as well as to improve recovery from neurodegenerative diseases.

The application provides agents that promote neuronal regeneration and these agents may be used either alone, or may be used in combination with one or more agents promoting neuronal regeneration. Furthermore agents identified in the subject methods may be administered as part of a therapeutic regimen in combination with other agents such a neurotrophic factors or growth factor and/or enzymes which promote degradation of proteoglycan sugars in glial scars. Additionally, agents identified in the subject methods may be administered as part of a therapeutic regimen in combination with other methods used to treat the specific neuronal injury or neurodegenerative disease. For example, in the case of Parkinson's disease, C1 activators and/or C2 inhibitors may be administered in combination with L-dopa or other Parkinson's disease medication, or in combination with a cell based neuronal transplantation therapy for Parkinson's disease. In the case of an injury to the brain or spinal cord, C1 activators and/or C2 inhibitors may be administered in combination with physical therapy, hydrotherapy, massage therapy, and the like. In the case of peripheral neuropathy, as for example diabetic neuropathy, C1 activators and/or C2 inhibitors may be administered in combination with insulin.

C1 activators and/or C2 inhibitors can promote neuronal regeneration, even in the presence of the proteoglycans which compose glial rich scar tissue. Accordingly, the methods of the present application can be used to overcome the inhibitory effects of glial rich scar tissue, and thus be used to promote neuronal regeneration following tissue injury and/or degeneration, including tissue injury or degeneration which results in formation of a glial rich scar. The methods of the present application thus provide a novel treatment option for patients afflicted with any of a number of conditions which result in injury or degeneration of neuronal cells of the central and peripheral nervous system. Examples of conditions which can be treated by the methods described herein include, without limitation, spinal cord injury, brain injury (following surgery, stroke, cancer treatment, or trauma), peripheral nerve injury, Parkinson's disease, Huntington's disease, detached retina, macular degeneration, multiple sclerosis, Alzheimer's disease, amotrophic lateral sclerosis (ALS), peripheral neuropathy, and diabetic neuropathy. One of skill in the art will appreciate that injuries or conditions that results in damage to or degeneration of neurons are candidates for treatment with the compositions of the present application.

Exemplary Conditions which May be Treated by the Methods of the Present Invention.

a. Injury

A physical injury to cells of the CNS may result in glial scar formation which inhibits neuronal regeneration and thus interferes with recovery from the injury. Such injuries include physical injuries to cells of the CNS including cells of the brain, spinal cord and eye. Some physical injuries may not result in glial scar formation, but may still inhibit regeneration due to inflammation, trauma, and so on. Examples of physical injuries include, but are not limited to, crushing or severing of neuronal tissue, such as may occur following a fall, car accident, gun shot or stabbing wound, etc.

Further examples of an injury to cells of the CNS include those caused by infection such as by a bacterial or viral infection. Examples of bacterial or viral infections affecting cells of the CNS include meningitis, staph, and HIV. However, one of skill in the art will recognize that many different types of bacteria or viruses may infect cells of the CNS and cause injury.

Additionally, injury to cells of the CNS often occurs as a consequence or side effect of other treatments being used to relieve the effects of a condition of the CNS. For example, individuals often undergo surgery to relieve discomfort, numbness, and/or lack of mobility which results from a pinched nerve, bulging disk, etc. Such surgery may result in additional injury. Additional examples of surgeries involving cells of the CNS include brain surgery to relieve intracranial pressure, surgery to remove a malignant or benign tumor, surgery to treat an anuryism, surgery to insert a stent, intraluminal device, implant, etc. In the foregoing examples, injury following surgery may be the result of error on the part of the physician, or may be a normal side effect of the successful surgical procedure.

Other treatment regimens which may cause injury to cells of the CNS include cancer therapies. Chemotherapeutic agents, radiation therapy, and the like may do substantial injury not only to cancerous cells, but also to healthy cells.

In addition to injuries to cells of the central nervous system, injury of cells of the peripheral nervous system may result in the formation of scar tissue, inflammation, trauma, and the like, and such mechanisms may inhibit regeneration. Accordingly, the present invention contemplates that C1 activators and/or C2 inhibitors can be used to promote neuronal regeneration, including increase the rate and/or extent of neuronal regeneration, in neuronal cells of the peripheral nervous system.

b. Neurodegenerative Diseases

A wide range of neurodegenerative diseases cause extensive cell damage (i.e., injury) to cells of the CNS and PNS. Accordingly, neurodegenerative diseases are candidates for treatment using the described agents. Administration of a C1 activator and/or C2 inhibitor may promote neuronal regeneration in the CNS or PNS of a patient with a neurodegenerative disease, and the promotion of neuronal regeneration can ameliorate, at least in part, symptoms of the disease. Agents may be administered individually, in combination with other agents of the invention, or as part of a treatment regimen appropriate for the specific condition being treated. The following are illustrative examples of neurodegenerative conditions which may be treated using C1 activators and/or C2 inhibitors.

Parkinson's disease is the result of the destruction of dopamine-producing neurons of the substantia nigra, and results in the degeneration of axons in the caudate nucleus and the putamen degenerate. Although therapies such as L-dopa exist to try to ameliorate the symptoms of Parkinson's disease, to date we are unaware of treatments which either prevent the degeneration of axons and/or increase neuronal regeneration. Administration of agents with promote neuronal regeneration can help to ameliorate at least certian symptoms of Parkinson's disease including rigidity, tremor, bradykinesia, poor balance and walking problems.

Alzheimer's disease, a debilitating disease characterized by amyloid plaques and neurofibrillary tangles, results in a loss of nerve cells in areas of the brain that are vital to memory and other mental abilities. There also are lower levels of chemicals in the brain that carry complex messages back and forth between nerve cells. Alzheimer's disease disrupts normal thinking and memory. The incidence of Alzheimer's disease will only increase as the average life expectancy continues to rise around the world. One of the most notable features of Alzheimer's disease is that affected individuals can live for extended periods of time (ten or more years) while being in an extremely debilitated state often requiring round the clock care. Accordingly, the disease takes not only an enormous emotional toll, but also exacts a tremendous financial toll on affected individuals and their families. Therapies which improve neuronal function, for example neurite outgrowth, have substantial utility in improving the quality of life of Alzheimer's sufferers.

Huntington's disease is a degenerative disease whose symptoms are caused by the loss of cells in a part of the brain called the basal ganglia. This cell damage affects cognitive ability (thinking, judgment, memory), movement, and emotional control. Symptoms appear gradually, usually in midlife, between the ages of 30 and 50. However, the disease can also strike young children and the elderly. Huntington's disease is a genetic disorder. Although people diagnosed with the disease can often maintain their independence for several years following diagnosis, the disease is degenerative and eventually fatal. Currently, there are no treatments available to either cure or to ameliorate the symptoms of this disease. Furthermore, the onset of Huntington's disease is typically in middle-age (approx age 40), at a time when many people have already had children. Thus, people have usually passed this fatal genetic disorder to their off-spring before they realize that they are ill.

Amyotrophic lateral sclerosis (ALS), often referred to as "Lou Gehrig's disease," is a progressive neurodegenerative disease that attacks motor nerve cells in the brain and the spinal cord. Degeneration of motor neurons affect the ability of the brain to initiate and control muscle movement. With all voluntary muscle action affected, patients in the later stages of the disease become totally paralyzed, and eventually die.

Macular degeneration is a catch-all term for a number of different disorders that have a common end result: the light-sensing cells of the central region of the retina—the macula—malfunction and eventually die, with gradual decline and loss of central vision, while peripheral vision is retained. Most cases of macular degeneration are isolated, individual, occurrences, mostly in people over age 60. These types are called Age Related Macular Degeneration (AMD). More rarely however, younger people, including infants and young children, develop macular degeneration, and they do so in clusters within families. These types of macular degeneration are collectively called Juvenile Macular Degeneration and include Stargardt's disease, Best's vitelliform macular dystrophy, Doyne's honeycomb retinal dystrophy, Sorsby's fundus dystrophy, Malattia levintinese, Fundus flavimaculatus, and Autosomal dominant hemorrhagic macular dystrophy.

Multiple sclerosis (MS) is an illness diagnosed in over 350,000 persons in the United States today. MS is characterized by the appearance of more than one (multiple) areas of inflammation and scarring of the myelin in the brain and spinal cord. Thus, a person with MS experiences varying degrees of neurological impairment depending on the location and extent of the scarring. The most common characteristics of MS include fatigue, weakness, spasticity, balance problems, bladder and bowel problems, numbness, vision loss, tremor and vertigo. The specific symptoms, as well as the severity of these symptoms, varies from patient to patient and is largely determined by the particular location within the brain of the lesions.

MS is considered an autoimmune disease. Recent data suggest that common viruses may play a role in the onset of MS. If so, MS may be caused by a persistent viral infection or alternatively, by an immune process initiated by a transient viral infection in the central nervous system or elsewhere in the body. Epidemiological studies indicating the distribution of MS patients suggest that there is a triggering factor responsible for initiating onset of the disease. Without being bound by theory, it appears that some environmental factor, most likely infectious, must be encountered.

The incidence of MS is higher in North America and Europe and this geographic distribution is further suggestive of an environmental influence(s) underlying onset of MS. Additionally, MS is more prevalent in women than in men, and is more common amongst Caucasians than within either Hispanic or African-American populations. Interestingly, MS is extremely rare within Asian populations.

C1 activators and/or C2 inhibitors for use in the methods of the present invention, as well as agents identified by the subject methods may be conveniently formulated for administration with a biologically acceptable medium, such as water, buffered saline, polyol (for example, glycerol, propylene glycol, liquid polyethylene glycol and the like) or suitable mixtures thereof. Optimal concentrations of the active ingredient(s) in the chosen medium can be determined empirically, according to procedures well known to medicinal chemists. As used herein, "biologically acceptable medium" includes solvents, dispersion media, and the like which may be appropriate for the desired route of administration of the one or more agents. The use of media for pharmaceutically active substances is known in the art. Except insofar as a conventional media or agent is incompatible with the activity of a particular agent or combination of agents, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Methods of introduction may also be provided by rechargeable or biodegradable devices. Various slow release polymeric devices have been developed and tested in vivo in recent years for the controlled delivery of agents, including proteinacious biopharmaceuticals. A variety of biocompatible polymers (including hydrogels), including both biodegradable and non-degradable polymers, can be used to form an implant for the sustained release of an agent at a particular target site. Delivery of agents to injury site can be attained by vascular administration via liposomal or polymeric nano- or micro-particles; slow-release vehicles implanted at the site of injury or damage; osmotic pumps implanted to deliver at the site of injury or damage; injection of agents at the site of injury or damage directly or via catheters or controlled release devices; injection into the cerebro-spinal fluid.

The agents identified using the methods of the present invention may be given orally, parenterally, or topically. They are of course given by forms suitable for each administration route. For example, they are administered in tablets or capsule form, by injection, inhalation, ointment, controlled release device or patch, or infusion.

One or more agents may be administered to humans and other animals by any suitable route of administration. With regard to administration of agent to the brain, it is know in the art that the delivery of agents to the brain may be complicated due to the blood brain barrier (BBB). Accordingly, the application contemplates that agents may be administered directly to the brain cavity. For example, agents can be administered intrathecally or intraventricularly. Administration may be, for example, by direct injection, by delivery via a catheter, or by injection into the cerebrospinal fluid.

However, although the BBB may present an impediment to the delivery of agents to the brain, it is also recognized that many polypeptides and small organic molecules are able to cross the BBB following systemic delivery. Therefore, the current application contemplates that agents may be delivered either directly to the sight of injury in the CNS or PNS, or may be delivered systemically.

Actual dosage levels of the one or more agents may be varied so as to obtain an amount of the active ingredient which is effective to achieve a response in an animal. The actual effective amount can be determined by one of skill in the art using routine experimentation and may vary by mode of administration. Further, the effective amount may vary according to a variety of factors include the size, age and gender of the individual being treated. Additionally the severity of the condition being treated, as well as the presence or absence of other components to the individuals treatment regimen will influence the actual dosage. The effective amount or dosage level will depend upon a variety of factors including the activity of the particular one or more agents employed, the route of administration, the time of administration, the rate of excretion of the particular agents being employed, the duration of the treatment, other drugs, compounds and/or materials used in combination with the particular agents employed, the age, sex, weight, condition, general health and prior medical history of the animal, and like factors well known in the medical arts.

The one or more agents can be administered as such or in admixtures with pharmaceutically acceptable and/or sterile carriers and can also be administered in conjunction with other compounds. Such additional compounds may include factors known to influence the proliferation, differentiation or migration of neuronal cells. These additional compounds may be administered sequentially to or simultaneously with the agents for use in the methods of the present invention. Exemplary compounds known to influence neuronal cell behavior include neurotrophic factors or growth factors known to promote cell survival. Such neurotrophic factors or growth factors include, without limitation, nerve growth factor (NGF), basic fibroblast growth factor (bFGF), brain-derived growth factor (BDGF), neurotrophin 3 (NT-3), neurotrophin 4 (NT-4), neurotrophin 5 (NT-5), glial derived neurotrophic factor (GDNF), and ciliary neurotrophic factor (CNTF).

In addition to the administration of the subject agents (e.g., agents which promote the "on" state of Class I Rho family GTPases or promote the "off" state of Class II Rho family GTPases) in combination with one or more neurotrophic factors or growth factors, the invention further contemplates that the subject agents can be administered in combination with one or more enzymes which digest proteoglycan sugars. Such enzymes act on the proteoglycans which comprise the glial scar, and help to decrease the physical and/or molecular barrier imposed by this glial scar.

Agents can be administered alone, or can be administered as a pharmaceutical formulation (composition). Said agents may be formulated for administration in any convenient way for use in human or veterinary medicine. In certain embodiments, the agents included in the pharmaceutical preparation may be active themselves, or may be a prodrug, e.g., capable of being converted to an active compound in a physiological setting.

Thus, another aspect of the present invention provides pharmaceutically acceptable compositions comprising an effective amount of one or more agents, formulated together with one or more pharmaceutically acceptable carriers (additives) and/or diluents. As described below, the pharmaceutical compositions of the present invention may be specially formulated for administration in solid or liquid form, including those adapted for the following: (1) local administration to the central nervous system, for example, intrathecal, intraventricular, intraspinal, or intracerebrospinal administration (2) oral administration, for example, drenches (aqueous or non-aqueous solutions or suspensions), tablets, boluses, powders, granules, pastes for application to the tongue; (3) parenteral administration, for example, by subcutaneous, intramuscular or intravenous injection as, for example, a sterile solution or suspension; (4) topical application, for example, as a cream, ointment or spray applied to the skin; or (5) opthalamic administration, for example, for administration following injury or damage to the retina. However, in certain embodiments the subject agents may be simply dissolved or suspended in sterile water. In certain embodiments, the pharmaceutical preparation is non-pyrogenic, i.e., does not elevate the body temperature of a patient.

Some examples of the pharmaceutically acceptable carrier materials that may be used include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, one or more agents may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of agent of the present invention. These salts can be prepared in situ during the final isolation and purification of the agents of the invention, or by separately reacting a purified agent of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the agents include the conventional nontoxic salts or quaternary ammonium salts of the agents, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the one or more agents may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of agents of the present invention. These salts can likewise be prepared in situ during the final isolation and purification of the agents, or by separately reacting the purified agent in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the agent which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent with the carrier and, optionally, one or more accessory ingredients. In general, the formulations are prepared by uniformly and intimately bringing into association an agent of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a agent of the present invention as an active ingredient. An agent of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or a cacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the agents of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agents, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Transdermal patches have the added advantage of providing controlled delivery of an agent of the present invention to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the agent in a polymer matrix or gel.

Ophthalmic formulations, eye ointments, powders, solutions and the like, are also contemplated as being within the scope of this invention. These are particularly useful for injury and degenerative disorders of the eye including retinal detachment and macular degeneration.

Pharmaceutical compositions of this invention suitable for parenteral administration comprise one or more agents of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of an agent, it is desirable to slow the absorption of the agent from subcutaneous or intramuscular injection. This may be accomplished by the use of a liquid suspension of crystalline or amorphous material having poor water solubility. The rate of absorption of the agent then depends upon its rate of dissolution which, in turn, may depend upon crystal size and crystalline form. Alternatively, delayed absorption of a parenterally administered agent form is accomplished by dissolving or suspending the agent in an oil vehicle.

EXEMPLIFICATION

The invention now being generally described, it will be more readily understood by reference to the following examples which are included merely for purposes of illustration of certain aspects and embodiments of the present invention, and are not intended to limit the invention.

Example 1

Three-Dimensional Agarose Gel for Examining Neuronal Growth

Several in vitro systems exist to examine the growth of neurons in response to inhibitory or growth promoting effects. For example, two dimensional and three dimensional astrocyte cultures can be used to mimic the effect of an injury, and thus can be used to measure neuronal regeneration following injury (Snow et al. (1990) *Experimental Neurology* 109: 111-130; Fawcett et al. (1989) *Developmental Biology* 135: 449-458; Fok-seang et al. (1995) *Brain Research* 689: 207-223). However, these systems make it difficult to separate the pleiotrophic effects exerted by astrocytes.

We have designed a three dimensional agarose gel system which does not include astrocytes, and have demonstrated that it can be effectively used to examine inhibitory effects on neuronal growth and behavior (Yu and Bellamkonda (2001) *Journal of Neuroscience Research* 66: 303-310). Additionally, this system is especially amenable as a tool to screen for agents which can promote neuronal regeneration (e.g., agents which can overcome an inhibitory effect, such as that exerted by chondroitin sulfate GAGs).

FIG. 1 provides a diagram of the multilayer three-dimensional agarose gel. This three-dimensional system allows observation of neuronal cell behavior at gel interfaces. In this example, layer 1 is a control interface composed of 1% agarose, layer 2 contains the neuronal explant, in this case an explant of dorsal root ganglia (DRG) in 1% agarose, and layer 3 is 2% agarose containing chondroitin sulfate-B. The layer 1/layer 2 interface provides a control agarose/agarose interface, while the layer 2/layer 3 interface provides an agarose/CS-GAG rich agarose interface. The ability of neurites to cross the interface between layer 2/layer 3 can be measured. Although in this example, layer 3 contains CS-GAG, it can contain any substance that effects neuronal growth or behavior.

This method can also be performed as a single layer three dimensional gel containing the inhibitory substance.

Not only is this assay useful for measuring the behavior of neurons in the presence of inhibitory substances like chondroitin sulfate GAGs, but it is also useful to screen for agents which can overcome, in whole or in part, the effects of an inhibitory substance. For example, neurons can be exposed to an agent, and the ability of that agent to promote neuronal regeneration can be measured. In another example, compounds which may decrease the inhibitory effect of layer 3 can be added to layer 3. In another example, neurons can be exposed to an agent in combination with the addition of a compound to layer 3.

Methods:

Agarose gels were made by dissolving SeaPrep agarose (FMC Corp) in pH 7.4 PBS. Agarose solutions were sterilized by passing through a 0.45 u m filter, gelled and stored at 4° C. Prior to use, the gels were degelled at 65° C., cooled to 37° C., and gelled.

For construction of three dimensional system, agarose gels were layered in a rectangular culture dish. 1% liquid agarose was poured into the dish, and chilled to allow layer 1 to gel. After layer 1 had gelled, liquid agarose containing several E9 chick DRG were poured onto layer 1, and chilled to form layer 2. After layer 2 had gelled, 2% liquid agarose containing chondroitin sulfate-B was poured onto layer 2 and chilled to form layer 3.

To maintain the cells in this culture system, culture medium consisting of DMEM supplemented with 10% fetal bovine serum, 1% penicillin-streptomycin, and 50 ng/mL nerve growth factor was added to the top of the gel. The dish containing the three-dimensional layers was manintained at 37° C. with 95% humidity and 5% $CO_2$.

Example 2

Modulation of Chondroitin Sulfate GAGs Overcomes Inhibition of Neuronal Growth

The three-dimensional culture system summarized in Example 1 provides a method for assessing the effect of inhibitory substances like chondroitin sulfate GAGs on neuronal growth. The ability of neuronal cells to extend processes across the interfaces was quantified by determining the percentage of neurites that successfully crossed the interface using light microscopy. Both embryonic chick DRG and retinal ganglia extended processes in 3D in agarose hydrogels, and no significant difference in growth cone crossing was observed between 1:1% or 1:2% (wt/vol) agarose gels in the absence of CS-GAGs.

Figure 2:
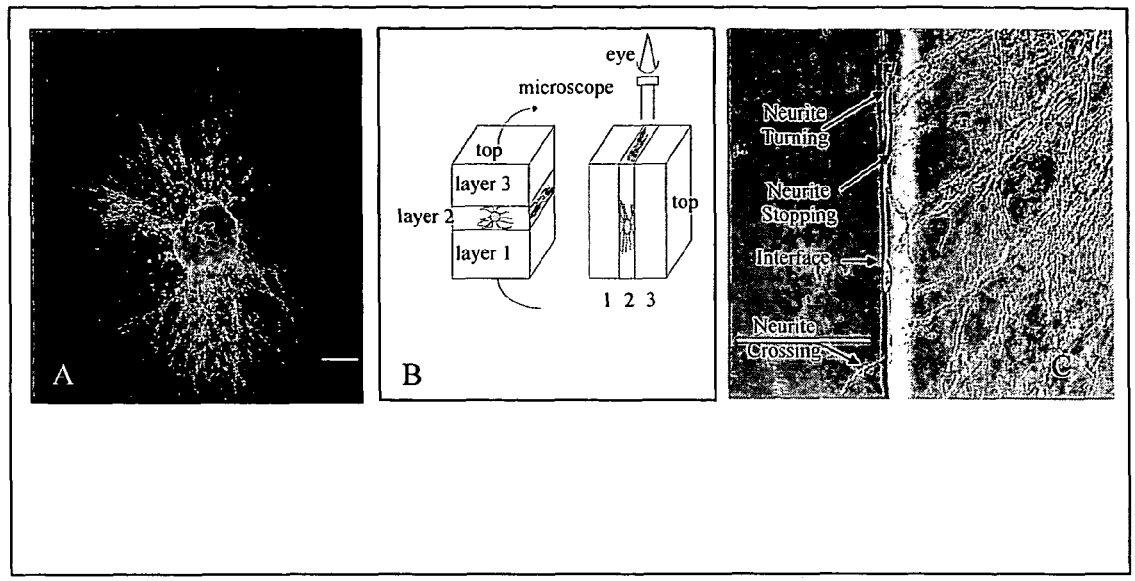
FIG. 2 shows the behavior of chick DRG cultured in the three-dimensional agarose gel culture system.
Figure 3:
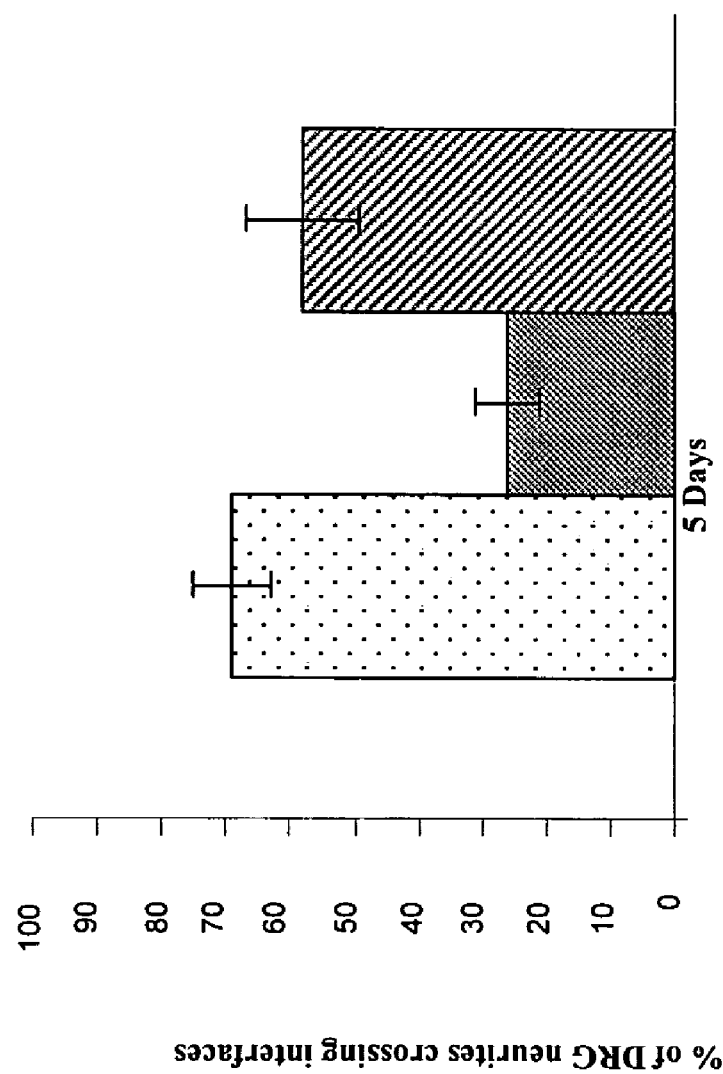
FIG. 3 shows a graph summarizing the behavior of E9 chick DRG cultured in three-dimensional gel. The bars indicate the percentage of DRG neuronal processes that cross the interface between 2 layers in the three dimensional gel under various conditions. The left most bar is a control indicating that approximately 70% of neurites cross the interface between a layer of 1% agarose and a layer of 2% agarose. The middle bar indicates the statistically significant decrease in the percentage of neurites capable of crossing the interface between 1% agarose and 2% agarose modified with chondroitin-sulfate B. The right most bar indicates a statistically significant restoration in the ability of neurites to cross an interface of 1% agarose and 2% agarose modified with CS-4 following treatment of the gel with chondro-4-sulfatase.

The ability of E9 chick dorsal root ganglion neurons (DRGs) to cross a non-CS-GAG containing interface was observed under light microscopy and approximately 65-75% of the neurites crossed this interface. When CS-GAG rich interfaces were used DRG neurite extension across the interface was significantly inhibited compared to non-GAG containing gels (FIGS. 2-3). To ensure that the inhibition was CS-GAG mediated, the CS-GAG gels were digested with chondroitinase. The inhibitory effect was abolished when CS-GAG sulfate groups were removed selectively using chondroitinase (chondro-4-sulfatase, FIG. 3).

Briefly, FIG. 2 shows the behavior of chick DRG cultured in the three-dimensional agarose gel culture system. FIG. 2A shows an E9 Chick DRG extending processes in a 3D agarose gel culture. FIG. 2B summarizes the three-dimensional agarose gel culture system outlined in detail in FIG. 1 and in Example 1. FIG. 2C shows that neuronal growth from E9 chick DRG was inhibited at the 3D interface between layer 2 and layer 3 containing chondrotin sulfate. Specifically, neuronal processes from DRGs cultured in layer 2 (1% agarose) extend, however this extension is inhibited when the processes contact the layer 2/layer 3 interface where the layer 3 interface contains 2% agarose modified with chondroitin sulfate B. The results of these studies are summarized graphically in FIG. 3. The bars indicate the percentage of DRG neurites which cross the interface between 2 layers in the three dimensional gel under various conditions. The left most bar is a control indicating that approximately 65-75% of neurites cross the interface between a layer of 1% agarose and a layer of 2% agarose. The middle bar indicates the statistically significant decrease in the percentage of neurites capable of crossing an interface of 1% agarose and 2% agarose modified with chondroitin-sulfate 4 (CS-4). The right most bar indicates a statistically significant restoration in the ability of neurites to cross an interface of 1% agarose and 2% agarose modified with CS-4 following treatment of the gel with chondro-4-sulfatase.

Example 3

Figure 4:
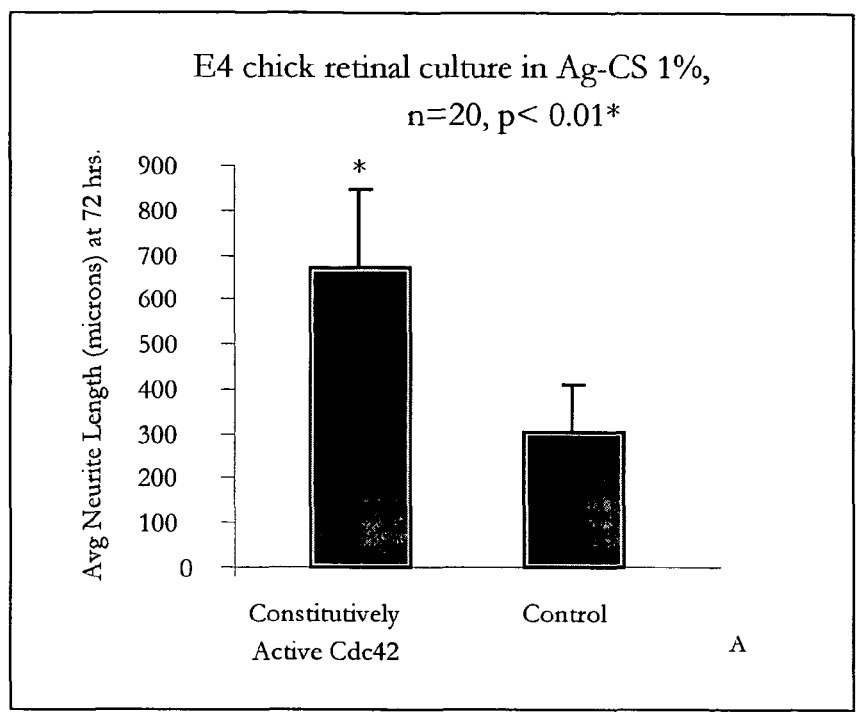
FIG. 4 shows the effect of activation of a Rho family GTPase on promoting neurite extension.
Figure 4:
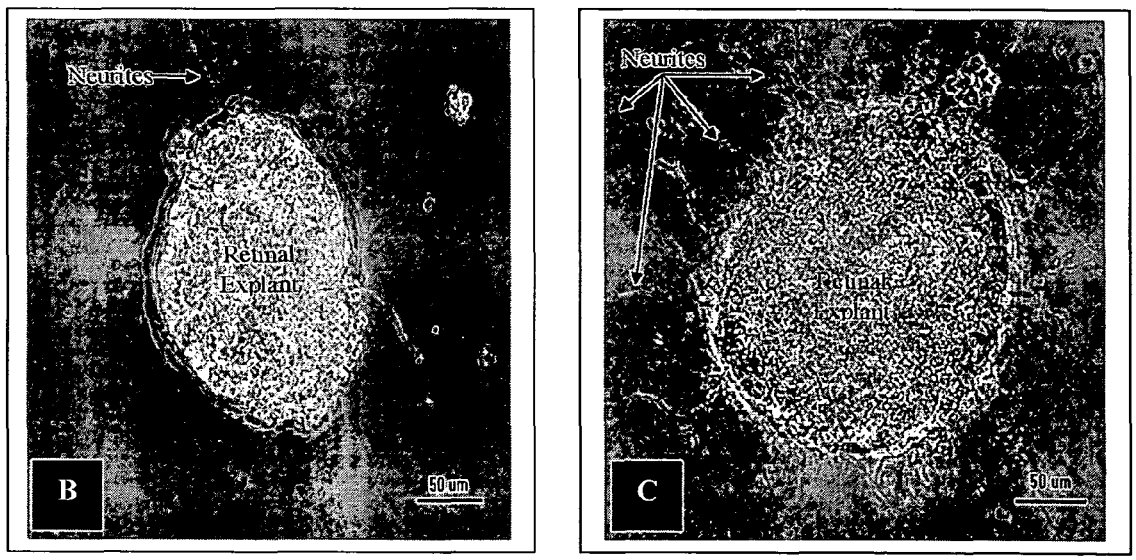

Modulation of Rho Family GTPase Activity Overcomes CS-GAG Inhibition of Neuronal Growth Retrovirus encoding constitutively active Cdc42 was added to E4 chick retinal ganglion cell cultures. The length of the processes which extend from the explant was measured in a CS-GAG modified agarose gel. Retinal ganglion cells expressing constitutively active Cdc42 displayed significantly longer neurites than control uninfected cultures after 72 hours (FIG. 4). This demonstrates that activation of Rho family GTPases facilitate neuronal regeneration, and that this regeneration can occur in the presence of inhibitory molecules.

FIG. 4 shows the effect of activation of a Rho family GTPase on promoting neuronal regeneration. E4 chick retina was cultured in a single layer three dimensional gel containing chondroitin sulfate GAG modified agarose. The length of the processes extending from the explant was measured. The right most bar indicates that retina cultured in chondroitin sulfate GAGs extend only short processes. The left most bar indicates that infection of E4 chick retina with retrovirus encoding constitutively active Cdc42 significantly increases the length of the process in the presence of chondroitin sulfate. For this experiment, the constitutively active Cdc42 protein used was the Q61L mutation of human Cdc42 (Q61L mutation of SEQ ID NO: 2).

Example 4

Two Dimensional System for Examining Neuronal Regeneration

We developed a two-dimensional model to observe the effects of substrate-bound GAGs or CSPGs on neurite extension. Briefly, the surfaces of glass coverslips were modified using 3-aminopropyltriethoxysilane, which binds amines to the surface. Through a two-step covalent coupling procedure, chondroitin sulfate C(CS-C) was crosslinked to the amines on the surface of the coverslip. First, CS-C was linked to EDAC, a zero-length crosslinker, that reacts with amine groups. With the aid of the Bonhoeffer matrix the CS-C-EDAC solution was passed into the microchannels incubated at room temperature for 30 minutes and removed. This process was repeated three additional times with fresh CS-C-EDAC solution. The CS-C covalently couple to the amines on the modified coverslip via the EDAC.

The coverslips were sonicated for 5 minutes to remove any CS-C that was not covalently bound to the coverslip. The coverslips were sterilized in 70% ethanol, and 15,000 cells were seeded on top of the micropatterned area and incubated at 37° C., 5% $CO_2$. The behavior of the seeded cells can now be examined in the presence or absence of agents which either influence the cells themselves (e.g., Class I activators, Class II inhibitors, etc.) or agents which alter the CS-C. Since the coverslip consists of alternating rows of CS-C, the ability of cells to extend processes along the short axis of the coverslip (from a CS-C non-containing to CS-C containing region) is a measure of the ability of the cells to extend processes across a CS-C containing interface. This method can be easily adapted to assess the inhibitory role of other molecules by covalently linking such molecules to a coverslip as described above.

In another modification of this method, the substrate lane assay can be performed using slight modifications of the Bonhoeffer method (Vielmetter et al. (1990) Exp Brain Res 81: 283-287). Briefly, tissue culture dishes arecoated with nitrocellulose (Lagenaur and Lemmon (1987) PNAS 84: 7753-7757), dried and the silicon lane matrix was applied to the dish surface. The first substrate is injected into the channels of the matrix, incubated for 10 minutes, aspirated then replaced with a fresh aliquot of the same substrate for several cycles. All remaining binding sites within the lanes were blocked with bovine serum albumin (BSA-fraction V; Sigma) and the lanes were rinsed with calcium-magnesium free phosphate buffer (CMF). The matrix was removed and the lanes were dried briefly. The second substrate was spread across the lane area and incubated for 30 minutes. The entire dish was blocked with BSA, then rinsed with culture medium.

Neurites initiated growth on one substrate (a growth promoting substrate) and crossed onto the second substrate from the adjacent lanes. When given a choice between a growth promoting substrate and a growth inhibitory substrate (for example CS-GAGs), neurites grew exclusively on one substrate, with no initiation of growth or crossover onto the lanes containing the inhibitory substrate. Growth cones grew right up to the border between the two substrates and stalled, but did not cross over onto the inhibitory substrate.

Example 5

Figure 5:
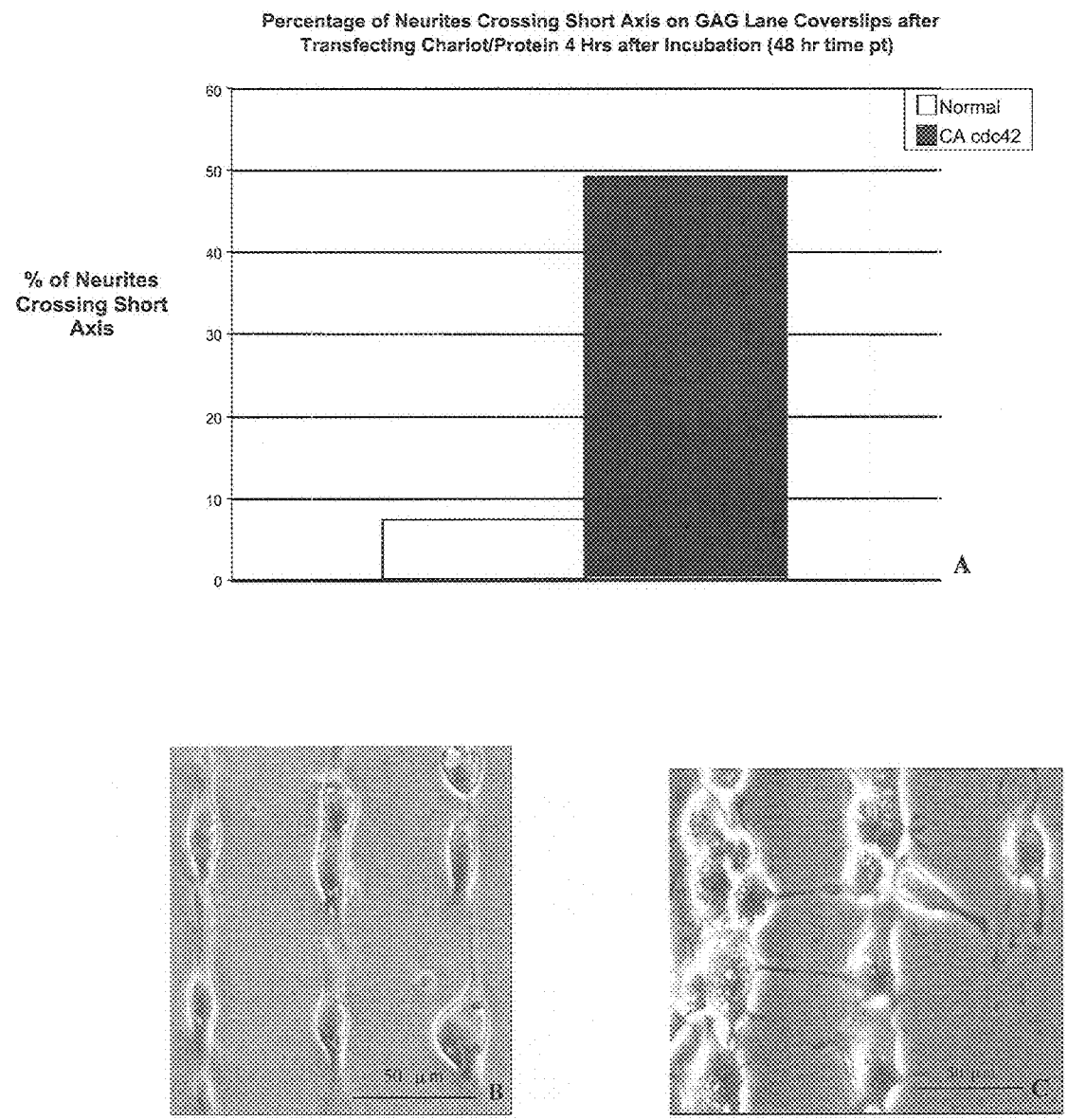
FIG. 5 summarizes the results of experiments which examined the neuronal growth of NG108 cells cultured on a two dimensional coverslip containing alternating stripes of chondroitin sulfate.

Modulation of Rho Family GTPase Activity Overcomes CS-GAG Inhibition of Neuronal Growth The chondroitin sulfate GAGs containing coverslips described in Example 4 were used to measure cell behavior on these coverslips following addition of a constitutively active Rho family GTPase. FIG. 5 summarizes the results of experiments which examine the neuronal growth of NC108 cells cultured on a two dimensional coverslip containing alternating stripes of chondroitin sulfate, FIG. 5A provides a graph which shows that less than 10% of unmodified NG108 cells cross the short axis of a chondroitin sulfate containing coverslip. However, approximately 50% of NG108 cells transfected with an activated Rho family GTPase (constitutively active Cdc42) cross the short axis. In these experiments, constitutively active Cdc42 protein was delivered to NC108 cells directly using the CHARIOT protein transduction system. FIG. 5B shows a picture (10× magnification) of unmodified NC108 cells approximately 48 hours after seeding of the cells onto the chondroitin sulfate GAGs containing coverslips. Note that the cells align along the long axis, and do not extend processes along the short axis. FIG. 5C shows a picture (10× magnification) of NG108 cells expressing constitutively active Cdc42. Note the extensive neuronal processes along the short axis.

Example 6

Construction of Viruses Expressing Rho Family GTPases

Construction and expression of the Rho family GTPase retroviruses: The retroviral system used is a tetracycline repressible promoter-based ("tet-off") system. This particular system allows both the regulatory protein and the gene of interest to be expressed from a single vector. All of the necessary packaging genes and tetracycline regulatory proteins are found in the pBPSTR1 plasmid. The retroviruses used for our studies were made by transfecting the PA317 helper cell line with the plasmids and thus we generated amphotrophic retroviruses that express various proteins. Using the pBP-STR1 vector, the following constructs were generated: dominant negative variant of the human isoforms of the Rho family GTPases (Tl7N Rac1, T19N RhoA, and T17N Cdc42) and the human isoforms of the constituitively active variants of the Rho family GTPases (Q61L Rac, Q63L Rho, and Q61 L Cdc42).

Recombinant HSV Preparation: The Herpes simplex virus type 1 was produced as previously described (Lim et al. (1996) Biotechniques 20: 60-69). Using the HSV-1 vectors pHSVpuc and pHSV-IRES-GFP, we generated new viral vectors containing extended multiple cloning sites (MCS), which we called pHSV-MCS and pHSV-IRES-GFP-MCS. We inserted the cDNAs encoding dominant negative forms of the human isoforms of the Rho family GTPases (Tl7N Rac1, T19N RhoA, and T17N Cdc42) and the human isoforms of the constituitively active forms of the Rho family GTPases (Q61L Rac, Q63L Rho, and Q61L Cdc42). The virus was produced by transfection of a helper cell line (2-2 vero cells), followed by infection with a helper virus (5dl1.2). Following three amplification cycles, the virus was purified using sucrose density ultracentrifugation.

Example 7

HSV-1 Infection of E8 Chick Retinal Explants

Chick E8 retinal explants contain postmitotic retinal ganglion cells. Thus the ability of HSV-1 to infect cells in such an explant can be used to assess the ability of HSV-1 to infect post mitotic cells.

Figure 6:
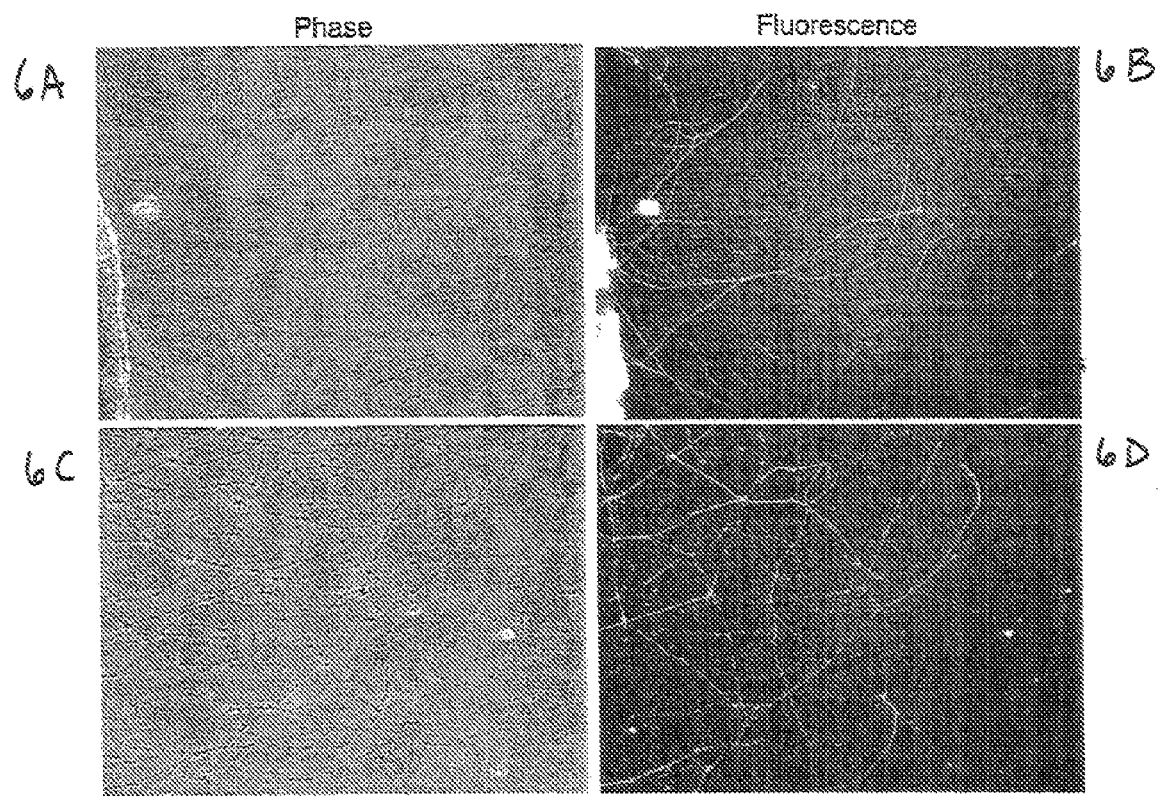
FIG. 6 shows neuronal growth of retinal ganglion cells on a laminin substrate. The post-mitotic retinal ganglion cells were infected with a replication-defective Herpes Simplex Virus type 1 encoding the green fluorescent protein (GFP).

Briefly, E8 chick retinal explants were cultured on a laminin coated substrate where they grow and extend processes (Halfter et al. (1983) *Developmental Biology* 95: 56-64; Drazba and Lemmon (1990) *Developmental Biology* 138: 82-93). These neurons were infected with a replication-defective Herpes Simplex Virus type 1 encoding the green fluorescent protein (GFP). Thus, expression of GFP in the neurons indicates that exogenous proteins can be expressed in post mitotic neurons using HSV-1 infection (FIG. 6).

Example 8

Alternative Two-Dimensional Model for Assessing Neurite Extension

We developed a second model to observe the effects of substrate-bound GAGs or CSPGs on neurite extension. Briefly, alternating lanes of the CSPG aggrecan and laminin were created on 60 mm diameter tissue culture dishes using a modified version of the Bonhoeffer method. Thus, neurite extension of cells across laminin/CSPG boundaries could be observed in these coated tissue culture dishes. Such laminin/CSPG coated dishes were used for the experiments summarized in the following examples and in FIGS. 7-10.

Example 9

Neurite Extension Following Transduction of C1 Activators or C2 Inhibitors

NG108-15 cells (available from ATCC, Manassas, Va.) were removed from culture flasks and resuspended in Neurobasal-A media (Invitrogen, Carlsbad, Calif.) supplemented with N-2, L-glutamine, and 1% penicillin/streptomycin. $2 \times 10^4$ NG108-15 cells were added to a laminin/CSPG coated dish as described in Example 8. After approximately 4 hours, the cells formed lanes adhering to the laminin lanes. The ability of the cells to migrate and/or extend processes across the laminin/CSPG boundary was then assessed following transduction of the cells with control proteins, with various Class I activator proteins, or with a Class 2 inhibitor protein.

Cells were transduced using the CHARIOT protein transduction system with any one of the following: GST control alone, activated Cdc42-GST, dominant negative Cdc42-GST, activated Rac1-GST, dominant negative Rac1-GST, activated RhoA-GST, or the RhoA inhibitor C3 transferase (Cytoskeleton, Denver, Colo.). The activated and dominant negative variants used for these experiments were as following: activated Cdc42=Q61L Cdc42, dominant negative Cdc42=T17N Cdc42, activated Rac1=Q61L Rac1, dominant negative Rac1=T17N Reel, activated RhoA=Q63 L RhoA. Following protein transduction, cells were placed in humidified incubators at 37° C., and 5% $CO_2$ and were imagined after 48 hours.

Figure 7:
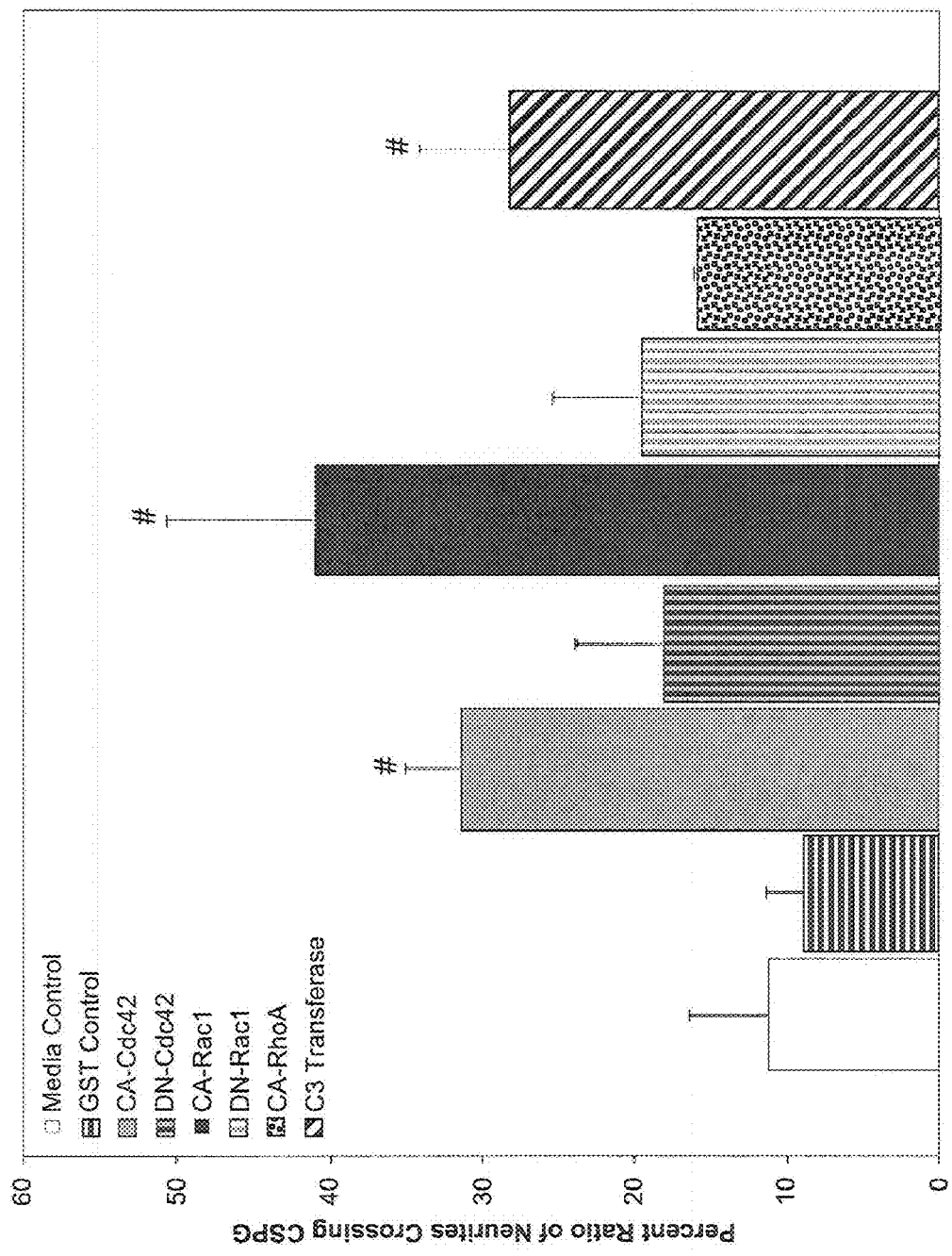
FIG. 7 summarizes the results of experiments which measured the percentage of neurites that cross a laminin/aggrecan border following transduction of NG108-15 cells with either control proteins or with C1 activator or C2 inhibitor protein. Neurites were transduced with either control media, GST alone, constitutively active Cdc42, dominant negative Cdc42, constitutively active Rac1, dominant negative Rac1, constitutively active RhoA, or the RhoA inhibitor (e.g., C2 inhibitor) C3 transferase. Note that transduction with constitutively active Cdc42, constitutively active Rac1, or the RhoA inhibitor C3 transferase all result in a statistically significant increase in the percentage of neurites that cross a laminin/aggrecan boundary in comparison to controls.

FIG. 7 summarizes the results of these experiments. Briefly, we observed a statistically significant (statistically significant changes indicated with the # symbol) increase in the percentage of cells crossing the laminin/CSPG boundary in cells transduced with either activated Cdc42, activated Rac1, or the RhoA inhibitor C3 transferase (e.g., cells transduced with a Class 2 inhibitor). This statistically significant increase is in comparison to cells that were either not transduced with protein or were transduced with GST alone. Additionally, the results in FIG. 7 indicated, as contemplated throughout the present application, that transduction of cells with either dominant negative Cdc42, dominant negative Rac1, or activated RhoA did not significantly promote neurite extension across laminin/CSPG boundaries.

Example 10

Dose Dependence

Figure 8:
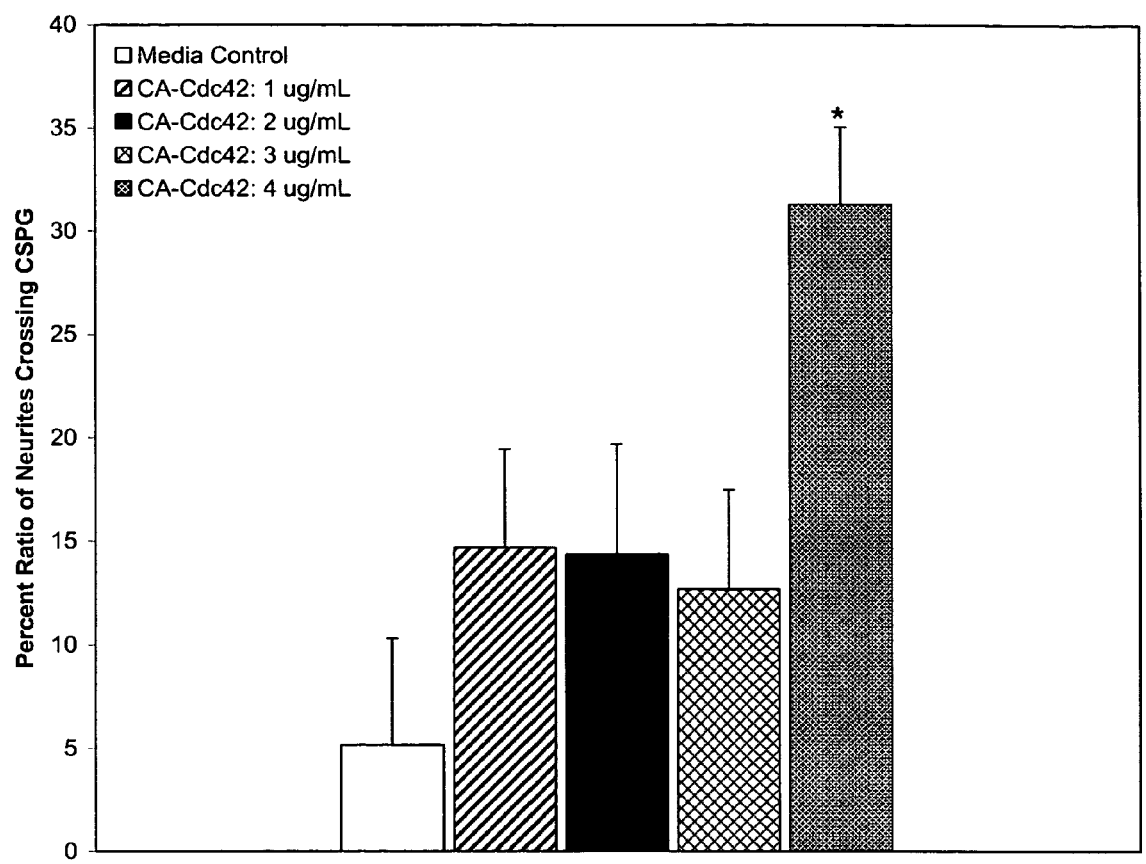
FIG. 8 summarizes results of experiments that examined neurite crossing of laminin/aggrecan boundaries following transduction of NG108-15 cells with various concentrations of constitutively active Cdc42. Neurites were transduced with either control media, or increasing concentrations (1 µg/mL, 2 µg/mL, 3 µg/mL, or 4 µg/mL) of constitutively active Cdc42. Note that transduction of 4 µg/mL of constitutively active Cdc42 resulted in a statistically significant increase in the percentage of neurites that cross a laminin/aggrecan boundary in comparison to controls.

FIG. 8 summarizes experiments designed to examine the dose dependence of the effect of a C1 activator on neurite extension across a laminin/CSPG boundary. Briefly, NG108-15 cells were cultured and dated as described in Example 9. The cells were transduced using CHARIOT with various concentrations of activated Cdc42. Cells were transduced with either 1 μg/mL, 2 μg/mL, 3 μg/mW or 4 μg/mL activated Cdc42 and neurite extension was observed in comparison to untransduced cells. As indicated in FIG. 8, there was a dose dependent increase in neurite extension upon transduction of activated Cdc42, and transduction of 4 μg/mL activated Cdc42 resulted in a statistically significant increase in neurite extension in comparison to untransduced cells. Note that a statistically significant change is indicated with an asterisk.

Example 11

Protein Transduction

Figure 9:
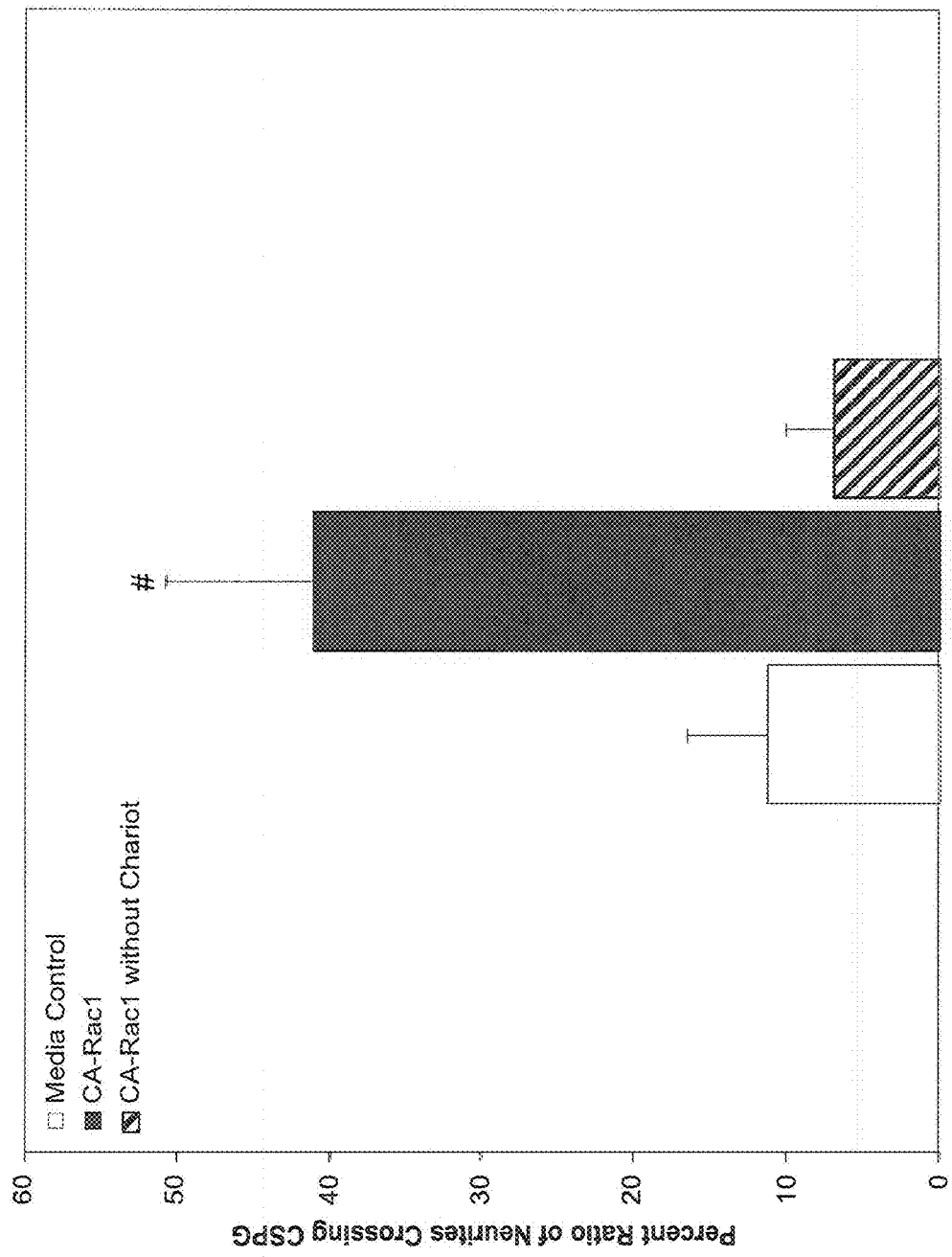
FIG. 9 summarizes results of experiments that examined neurite crossing of laminin/aggrecan boundaries following transduction of NG108-15 cells with constitutively active Rac-1 in the presence or absence of Chariot™. Note the statistically significant increase in the percentage of neurites that cross a laminin/aggrecan boundary in comparison to controls when cells are transduced with constitutively active Rac1 in the presence of Chariot™.

FIG. 9 summarizes experiments designed to examine the efficacy of the CHARIOT protein transduction system in promoting transduction of Rho family GTPases. Briefly, NF108-15 cells were cultured and plated as described in Example 9. The cells were transduced with activated Rac1 in either the presence or absence of CHARIOT and neurite extension was observed in comparison to untranaduced cells. As indicated in FIG. 9, under these conditions, the use of a protein transduction reagent like CHARIOT facilitated transduction of the protein into the cells. We observed a statistically significant (indicated by the # sign) increase in neurite extension when cells were transduced with activated Rac1 in the presence of CHARIOT in comparison to untransduced cells. We note, however, that the need for a protein transduction reagent may be overcome in whole or in part by using larger concentrations of protein or by modulating other culture conditions.

Figure 10:
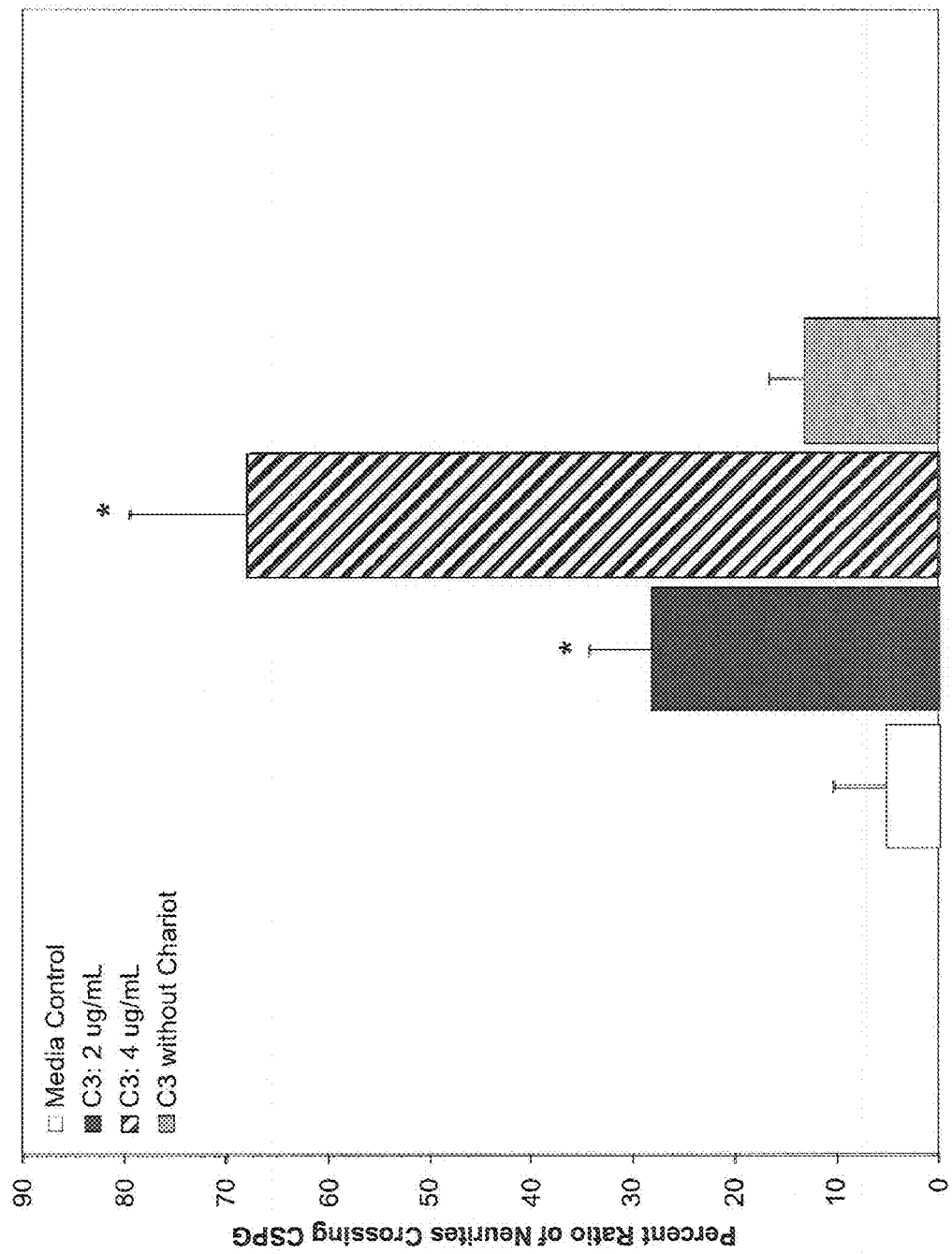
FIG. 10 summarizes results of experiments that examined neurite crossing of laminin/aggrecan boundaries following transduction of NG108-15 cells with various concentrations of the RhoA inhibitor (e.g., a C2 inhibitor) C3 transferase in the presence or absence of Chariot™. Note the statistically significant and dose dependent increase in the percentage of neurites that cross a laminin/aggrecan boundary in comparison to controls when cells are transduced with C3 transferase in the presence of Chariot™.

FIG. 10 examines the issues of dose responsiveness for the RhoA inhibitor (a Class 2 inhibitor) C3 transferase. As observed in FIG. 7, C3 transferase promotes neurite extension across a laminin/CSPG boundary, and the results summarized in FIG. 10 indicate that the effects of C3 transferase on these cells is dose dependent. We observed a statistically significant (indicated with an asterisk) increase in neurite extension when cells were transduced with either 2 μg/mL of C3 transferase or 4 μg/mL of C3 transferase, and this increase in neurite extension was dose dependent.

ADDITIONAL REFERENCES

WO99/23113 WO99/08533
Nobes and Hall (1995) *Cell* 81:53-62.
Luo et al. (1994) *Genes & Development* 8: 1787-1802.
Zipkin et al. (1997) *Cell* 90: 883-894.
Hall (1996) *Ann Rev Cell Biol* 10: 31-54.
Yu (2001) *Journal of Neuroscience Research* 66: 303-310.
Stichel and Muller (1998) *Cell Tissue Research* 294: 1-9.
Qiu et al. (2000) *Glia* 29: 166-174.
Margolis and Margolis (1997) *Cell Tissue Research* 290: 343-348.
Kaibuchi et al. (1999) *Annual Review of Biochemistry* 68: 459-486.
Nikolic (2002) *International Journal of Biochemistry and Cell Biology* 34: 731-745.
Ridley (2001) *Journal of Cell Science* 114: 2713-2722.
Barker et al. (1996) *Exp. Neurol.* 141: 79-93.
Davies et al. (1997) *Nature* 390: 680-683.
Grumet et al. (1996) *Perspect. Dev. Neurobiol.* 3: 319-330.
Burg et al. (1996) *J. Biol. Chem.* 271: 26110-26116.
Zuo et al. (1998) *Exp. Neurol.* 154: 654-662.
Moon et al. (2001) *Nat. Neurosci.* 4: 465-466.
Fidler et al. (1999) *J. Neurosci.* 19: 8778-8788.
Hoffman-Kim et al. (1998) *J Neurosci.* 18: 5881-5890.
Bradbury et al. (2002) *Nature* 416: 636-640.
Condic and Lemons (2002) *Neuroreport* 13: A37-48.
Dergham et al. (2002) *Journal of Neuroscience* 22: 6570-6577.
Fawcett and Asher (1999) *Brain Res. Bull.* 49: 377-391.
Fournier et al. (2003) *Journal of Neuroscience* 23: 1416-1423.
Hall. (1998) *Science* 279: 509-514.
Kottis et al. (2002) *Journal of Neurochemistry* 82: 1566-1569.
Luckenbill-Edds (1997) *Brain Res. Rev.* 23: 1-27.
McKeon et al. (1995) *Exp. Neurology* 136: 32-43.
McKerracher et al. (1994) *Neuron* 13: 805-811.
Monnier et al. (2003) *Mol Cell Neuroscience* 22: 319-330.
Morgenstern et al. (2002) *Prog Brain Research* 137: 313-332.
Mukhopadhyay et al. (1994) *Neuron* 13: 757-767.
Niederost et al. (2002) *Journal of Neuroscience* 22: 10368-10376.
Sango et al. (2003) *Exp Neurol* 182: 1-11.
Schmalfeldt et al. (2000) *Journal of Cell Science* 113: 807-816.
Tang. (2003) *Neurochem Int* 42: 189-203.

EQUIVALENTS

Those skilled in the art will recognize, or be able to ascertain using no more than routine experimentation, many equivalents to the specific embodiments of the invention described herein. Such equivalents are intended to be encompassed by the following claims.

---

The invention claimed is:

1. A method of treating an injury or degeneration of neuronal cells by promoting neuronal regeneration of the central or peripheral nervous system of a mammal, comprising administering an agent to at least one neural cell of the mammal, wherein the neural cell is in contact with at least one neuronal regeneration inhibitory substance of a glial scar in an amount effective to promote neuronal regeneration, the agent being selected from the group consisting of a Class I Rho family GTPase or a constitutively active Class I Rho family GTPase, wherein the Class I Rho family GTPase or constitutively active Class I Rho family GTPase is selected from the group consisting of Rac and Cdc42, and wherein the neuronal regeneration inhibitory substance comprises at least one proteoglycan.

2. A method of promoting neuronal regeneration of a neural cell, wherein the neural cell is in contact with at least one neuronal regeneration inhibitory substance in a mammal, the method comprising: administering an agent locally to at least one neural cell of the mammal in contact with at least one neuronal regeneration inhibitory substance of a glial scar in an amount effective to promote neuronal regeneration, the agent comprising a Class I Rho family GTPase selected from the group consisting of a Rac and Cdc42, wherein the neuronal regeneration inhibitory substance comprises at least one proteoglycan.

3. The method of claim 2, the neural cell being adjacent to a glial scar.

4. The method of claim 2, wherein the agent is a Class I Rho family GTPase polypeptide, wherein said polypeptide is encoded by a nucleic acid sequence wherein said nucleic acid sequence is at least 95% identical to a nucleic acid sequence as set forth in any one of SEQ ID NOs: 1 and 3.

5. The method of claim 4, wherein the agent is a Class I Rho family GTPase polypeptide having an amino acid sequence that is at least 95% identical to an amino acid sequence as set forth in SEQ ID NO: 2.

6. The method of claim 2 wherein the Class I Rho family GTPase is a constitutively active Cdc42 variant consisting of a Q61 L mutation in SEQ ID NO: 2.

7. The method of claim 2 wherein the Class I Rho family GTPase is a constitutively active Cdc42 variant consisting of a G12V mutation in SEQ ID NO: 2.

8. The method of claim 2, further comprising administering a neurotrophic factor with the agent to the neural cell.

9. The method of claim 8, wherein the neurotrophic factor comprises a brain derived neurotrophic factor (BDNF).

\* \* \* \* \*

SEQUENCE LISTING

<160> NUMBER OF SEQ ID NOS: 6

<210> SEQ ID NO 1
<211> LENGTH: 576
<212> TYPE: DNA
<213> ORGANISM: Homo sapiens
<220> FEATURE:
<221> NAME/KEY: CDS
<222> LOCATION: (1)..(576)
<223> OTHER INFORMATION:

<400> SEQUENCE: 1

```
atg cag aca att aag tgt gtt gtt gtg ggc gat ggt gct gtt ggt aaa      48
Met Gln Thr Ile Lys Cys Val Val Val Gly Asp Gly Ala Val Gly Lys
1               5                   10                  15 aca tgt ctc ctg ata tcc tac aca aca aac aaa ttt cca tcg gaa tat      96
Thr Cys Leu Leu Ile Ser Tyr Thr Thr Asn Lys Phe Pro Ser Glu Tyr
                20                  25                  30 gta ccg act gtt ttt gac aac tat gca gtc aca gtt atg att ggt gga     144
Val Pro Thr Val Phe Asp Asn Tyr Ala Val Thr Val Met Ile Gly Gly
            35                  40                  45 gaa cca tat act ctt gga ctt ttt gat act gca ggg caa gag gat tat     192
Glu Pro Tyr Thr Leu Gly Leu Phe Asp Thr Ala Gly Gln Glu Asp Tyr
        50                  55                  60
```

```
gac aga tta cga ccg ctg agt tat cca caa aca gat gta ttt cta gtc      240
Asp Arg Leu Arg Pro Leu Ser Tyr Pro Gln Thr Asp Val Phe Leu Val
 65                  70                  75                  80 tgt ttt tca gtg gtc tct cca tct tca ttt gaa aac gtg aaa gaa aag      288
Cys Phe Ser Val Val Ser Pro Ser Ser Phe Glu Asn Val Lys Glu Lys
                 85                  90                  95 tgg gtg cct gag ata act cac cac tgt cca aag act cct ttc ttg ctt      336
Trp Val Pro Glu Ile Thr His His Cys Pro Lys Thr Pro Phe Leu Leu
            100                 105                 110 gtt ggg act caa att gat ctc aga gat gac ccc tct act att gag aaa      384
Val Gly Thr Gln Ile Asp Leu Arg Asp Asp Pro Ser Thr Ile Glu Lys
        115                 120                 125 ctt gcc aag aac aaa cag aag cct atc act cca gag act gct gaa aag      432
Leu Ala Lys Asn Lys Gln Lys Pro Ile Thr Pro Glu Thr Ala Glu Lys
130                 135                 140 ctg gcc cgt gac ctg aag gct gtc aag tat gtg gag tgt tct gca ctt      480
Leu Ala Arg Asp Leu Lys Ala Val Lys Tyr Val Glu Cys Ser Ala Leu
145                 150                 155                 160 aca cag aga ggt ctg aag aat gtg ttt gat gag gct atc cta gct gcc      528
Thr Gln Arg Gly Leu Lys Asn Val Phe Asp Glu Ala Ile Leu Ala Ala
                165                 170                 175 ctc gag cct ccg gaa act caa ccc aaa agg aag tgc tgt ata ttc taa      576
Leu Glu Pro Pro Glu Thr Gln Pro Lys Arg Lys Cys Cys Ile Phe
            180                 185                 190

<210> SEQ ID NO 2
<211> LENGTH: 191
<212> TYPE: PRT
<213> ORGANISM: Homo sapiens

<400> SEQUENCE: 2

Met Gln Thr Ile Lys Cys Val Val Val Gly Asp Gly Ala Val Gly Lys
  1               5                  10                  15

Thr Cys Leu Leu Ile Ser Tyr Thr Thr Asn Lys Phe Pro Ser Glu Tyr
                 20                  25                  30

Val Pro Thr Val Phe Asp Asn Tyr Ala Val Thr Val Met Ile Gly Gly
             35                  40                  45

Glu Pro Tyr Thr Leu Gly Leu Phe Asp Thr Ala Gly Gln Glu Asp Tyr
         50                  55                  60

Asp Arg Leu Arg Pro Leu Ser Tyr Pro Gln Thr Asp Val Phe Leu Val
 65                  70                  75                  80

Cys Phe Ser Val Val Ser Pro Ser Ser Phe Glu Asn Val Lys Glu Lys
                 85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
        115                 120                 125

Leu Ala Lys Asn Lys Gln Lys Pro Ile Thr Pro Glu Thr Ala Glu Lys
130                 135                 140

Leu Ala Arg Asp Leu Lys Ala Val Lys Tyr Val Glu Cys Ser Ala Leu
145                 150                 155                 160

Thr Gln Arg Gly Leu Lys Asn Val Phe Asp Glu Ala Ile Leu Ala Ala
                165                 170                 175

Leu Glu Pro Pro Glu Thr Gln Pro Lys Arg Lys Cys Cys Ile Phe
            180                 185                 190

<210> SEQ ID NO 3
```

<211> LENGTH: 579
<212> TYPE: DNA
<213> ORGANISM: Homo sapiens
<220> FEATURE:
<221> NAME/KEY: CDS
<222> LOCATION: (1)..(579)
<223> OTHER INFORMATION:

<400> SEQUENCE: 3

```
atg cag gcc atc aag tgt gtg gtg gtg gga gac gga gct gta ggt aaa      48
Met Gln Ala Ile Lys Cys Val Val Val Gly Asp Gly Ala Val Gly Lys
1               5                   10                  15 act tgc cta ctg atc agt tac aca acc aat gca ttt cct gga gaa tat      96
Thr Cys Leu Leu Ile Ser Tyr Thr Thr Asn Ala Phe Pro Gly Glu Tyr
                20                  25                  30 atc cct act gtc ttt gac aat tat tct gcc aat gtt atg gta gat gga     144
Ile Pro Thr Val Phe Asp Asn Tyr Ser Ala Asn Val Met Val Asp Gly
            35                  40                  45 aaa ccg gtg aat ctg ggc tta tgg gat aca gct gga caa gaa gat tat     192
Lys Pro Val Asn Leu Gly Leu Trp Asp Thr Ala Gly Gln Glu Asp Tyr
        50                  55                  60 gac aga tta cgc ccc cta tcc tat ccg caa aca gat gtg ttc tta att     240
Asp Arg Leu Arg Pro Leu Ser Tyr Pro Gln Thr Asp Val Phe Leu Ile
65                  70                  75                  80 tgc ttt tcc ctt gtg agt cct gca tca ttt gaa aat gtc cgt gca aag     288
Cys Phe Ser Leu Val Ser Pro Ala Ser Phe Glu Asn Val Arg Ala Lys
                85                  90                  95 tgg tat cct gag gtg cgg cac cac tgt ccc aac act ccc atc atc cta     336
Trp Tyr Pro Glu Val Arg His His Cys Pro Asn Thr Pro Ile Ile Leu
                100                 105                 110 gtg gga act aaa ctt gat ctt agg gat gat aaa gac acg atc gag aaa     384
Val Gly Thr Lys Leu Asp Leu Arg Asp Asp Lys Asp Thr Ile Glu Lys
            115                 120                 125 ctg aag gag aag aag ctg act ccc atc acc tat ccg cag ggt cta gcc     432
Leu Lys Glu Lys Lys Leu Thr Pro Ile Thr Tyr Pro Gln Gly Leu Ala
        130                 135                 140 atg gct aag gag att ggt gct gta aaa tac ctg gag tgc tcg gcg ctc     480
Met Ala Lys Glu Ile Gly Ala Val Lys Tyr Leu Glu Cys Ser Ala Leu
145                 150                 155                 160 aca cag cga ggc ctc aag aca gtg ttt gac gaa gcg atc cga gca gtc     528
Thr Gln Arg Gly Leu Lys Thr Val Phe Asp Glu Ala Ile Arg Ala Val
                165                 170                 175 ctc tgc ccg cct ccc gtg aag aag agg aag aga aaa tgc ctg ctg ttg     576
Leu Cys Pro Pro Pro Val Lys Lys Arg Lys Arg Lys Cys Leu Leu Leu
                180                 185                 190 taa                                                                  579
```

<210> SEQ ID NO 4
<211> LENGTH: 192
<212> TYPE: PRT
<213> ORGANISM: Homo sapiens

<400> SEQUENCE: 4

```
Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Gly
            35                  40                  45

Lys Pro Val Asn Leu Gly Leu Trp Asp Thr Ala Gly Gln Glu Asp Tyr
        50                  55                  60
```

```
Asp Arg Leu Arg Pro Leu Ser Tyr Pro Gln Thr Asp Val Phe Leu Ile
 65                  70                  75                  80

Cys Phe Ser Leu Val Ser Pro Ala Ser Phe Glu Asn Val Arg Ala Lys
             85                   90                  95

Trp Tyr Pro Glu Val Arg His His Cys Pro Asn Thr Pro Ile Ile Leu
            100                 105                 110

Val Gly Thr Lys Leu Asp Leu Arg Asp Lys Asp Thr Ile Glu Lys
            115                 120                 125

Leu Lys Glu Lys Leu Thr Pro Ile Thr Tyr Pro Gln Gly Leu Ala
    130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Val Lys Lys Arg Lys Arg Lys Cys Leu Leu Leu
            180                 185                 190

<210> SEQ ID NO 5
<211> LENGTH: 582
<212> TYPE: DNA
<213> ORGANISM: Homo sapiens
<220> FEATURE:
<221> NAME/KEY: CDS
<222> LOCATION: (1)..(582)
<223> OTHER INFORMATION:

<400> SEQUENCE: 5 atg gct gcc atc cgg aag aaa ctg gtg att gtt ggt gat gga gcc tgt      48
Met Ala Ala Ile Arg Lys Lys Leu Val Ile Val Gly Asp Gly Ala Cys
1               5                   10                  15 gga aag aca tgc ttg ctc ata gtc ttc agc aag gac cag ttc cca gag      96
Gly Lys Thr Cys Leu Leu Ile Val Phe Ser Lys Asp Gln Phe Pro Glu
            20                  25                  30 gtg tat gtg ccc aca gtg ttt gag aac tat gtg gca gat atc gag gtg     144
Val Tyr Val Pro Thr Val Phe Glu Asn Tyr Val Ala Asp Ile Glu Val
        35                  40                  45 gat gga aag cag gta gag ttg gct ttg tgg gac aca gct ggg cag gaa     192
Asp Gly Lys Gln Val Glu Leu Ala Leu Trp Asp Thr Ala Gly Gln Glu
    50                  55                  60 gat tat gat cgc ctg agg ccc ctc tcc tac cca gat acc gat gtt ata     240
Asp Tyr Asp Arg Leu Arg Pro Leu Ser Tyr Pro Asp Thr Asp Val Ile
65                  70                  75                  80 ctg atg tgt ttt tcc atc gac agc cct gat agt tta gaa aac atc cca     288
Leu Met Cys Phe Ser Ile Asp Ser Pro Asp Ser Leu Glu Asn Ile Pro
                85                  90                  95 gaa aag tgg acc cca gaa gtc aag cat ttc tgt ccc aac gtg ccc atc     336
Glu Lys Trp Thr Pro Glu Val Lys His Phe Cys Pro Asn Val Pro Ile
            100                 105                 110 atc ctg gtt ggg aat aag aag gat ctt cgg aat gat gag cac aca agg     384
Ile Leu Val Gly Asn Lys Lys Asp Leu Arg Asn Asp Glu His Thr Arg
        115                 120                 125 cgg gag cta gcc aag atg aag cag gag ccg gtg aaa cct gaa gaa ggc     432
Arg Glu Leu Ala Lys Met Lys Gln Glu Pro Val Lys Pro Glu Glu Gly
    130                 135                 140
```

```
                                    -continued aga gat atg gca aac agg att ggc gct ttt ggg tac atg gag tgt tca        480
Arg Asp Met Ala Asn Arg Ile Gly Ala Phe Gly Tyr Met Glu Cys Ser
145                 150                 155                 160 gca aag acc aaa gat gga gtg aga gag gtt ttt gaa atg gct acg aga        528
Ala Lys Thr Lys Asp Gly Val Arg Glu Val Phe Glu Met Ala Thr Arg
                165                 170                 175 gct gct ctg caa gct aga cgt ggg aag aaa aaa tct ggt tgc ctt gtc        576
Ala Ala Leu Gln Ala Arg Arg Gly Lys Lys Lys Ser Gly Cys Leu Val
            180                 185                 190 ttg tga                                                                 582
Leu

<210> SEQ ID NO 6
<211> LENGTH: 193
<212> TYPE: PRT
<213> ORGANISM: Homo sapiens

<400> SEQUENCE: 6

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
                20                  25                  30

Val Tyr Val Pro Thr Val Phe Glu Asn Tyr Val Ala Asp Ile Glu Val
            35                  40                  45

Asp Gly Lys Gln Val Glu Leu Ala Leu Trp Asp Thr Ala Gly Gln Glu
        50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu
```